US012715858B2

(12) United States Patent
Dai et al.

(10) Patent No.: US 12,715,858 B2
(45) Date of Patent: Aug. 25, 2026

(54) PYRIDAZINONE COMPOUNDS

(71) Applicant: INVENTISBIO CO., LTD., Shanghai (CN)

(72) Inventors: Xing Dai, Shanghai (CN); Yanqin Liu, Shanghai (CN); Yueheng Jiang, Shanghai (CN)

(73) Assignee: INVENTISBIO CO., LTD., Shanghai (CN)

( * ) Notice: Subject to any disclaimer, the term of this patent is extended or adjusted under 35 U.S.C. 154(b) by 631 days.

(21) Appl. No.: 18/023,241

(22) PCT Filed: Aug. 27, 2020

(86) PCT No.: PCT/CN2020/111605
§ 371 (c)(1),
(2) Date: Feb. 24, 2023

(87) PCT Pub. No.: WO2022/041026
PCT Pub. Date: Mar. 3, 2022

(65) Prior Publication Data

US 2023/0339911 A1 Oct. 26, 2023

(51) Int. Cl.
*C07D 403/12* (2006.01)

(52) U.S. Cl.
CPC ........ *C07D 403/12* (2013.01); *C07B 2200/13* (2013.01)

(58) Field of Classification Search
CPC .................................................... C07D 403/12
See application file for complete search history.

(56) References Cited

FOREIGN PATENT DOCUMENTS

| | | |
|---|---|---|
| WO | 2007/009913 | 1/2007 |
| WO | 2009/037172 | 3/2009 |
| WO | 2014/043706 | 3/2014 |
| WO | 2020/073974 | 4/2020 |

OTHER PUBLICATIONS

International Search Report dated May 27, 2021, for PCT/CN2020/111605, 5 pages.
Written Opinion of the ISA dated May 27, 2021, for PCT/CN2020/111605, 4 pages.

*Primary Examiner* — Brian E McDowell
(74) *Attorney, Agent, or Firm* — NIXON & VANDERHYE, PC

(57) ABSTRACT

Provided herein are compounds, in particular, Compound 1, and compositions useful for treating or preventing diseases or disorders that are modulated by thyroid hormone receptor agonists, such as non-alcoholic steatohepatitis (NASH) or non-alcoholic fatty liver disease (NAFLD).

1

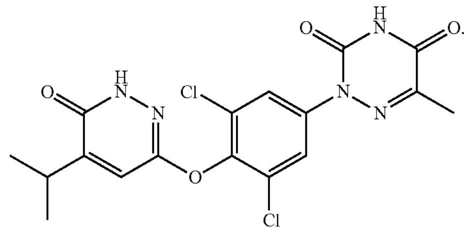

7 Claims, 12 Drawing Sheets

PYRIDAZINONE COMPOUNDS

This application is the U.S. national phase of International Application No. PCT/CN2020/111605 filed Aug. 27, 2020 which designated the U.S., the entire contents of which are hereby incorporated by reference.

BACKGROUND

In various embodiments, the present disclosure relates to thyroid hormone receptor agonists, pharmaceutical compositions, methods of preparing and methods of using the same, for example, for treating diseases or disorders such as nonalcoholic fatty liver disease and/or non-alcoholic steatohepatitis.

Background

Thyroid hormone (TH) plays a critical role in the human endocrine system and controls the energy metabolism through regulating the protein synthesis, carbohydrate and fat metabolism in liver, skeletal muscle and adipose tissue. In addition, TH affects cardiovascular, bone and renal functions. The activities of TH are mediated through its binding to thyroid hormones receptors (TRs), which include both isoforms of TRα and TRβ. TRα is primarily expressed in the brain and heart and to a lesser extent in kidney, skeletal muscle, lungs, whereas TRβ is predominantly expressed in the liver, kidneys and at lower levels in brain, heart, thyroid, skeletal muscle, lungs, and spleen. Therefore, TRα mainly affects the heart function, whereas TRβ controls carbohydrate and lipid metabolism in the liver.

TH regulates the energy expenditure through both central and peripheral actions. It maintains basal metabolic rate, facilitates adaptive thermogenesis, modulates appetite and food intake, and regulates body weight. Upon binding to thyroid hormones, TRs bind to the thyroid hormone response elements (TREs) of their downstream target genes to activate gene expression and hence the TR signaling pathway. In the absence of hormone, transcriptional regulation is blocked through TRs' association with co-repressors.

Non-alcoholic fatty liver disease (NAFLD) is a global epidemic with an incidence of 30% or more among adults in both developed and developing countries. NAFLD is considered to be a hepatic manifestation of the metabolic syndrome and is closely associated with the development of other metabolic risk factors such as type 2 diabetes mellitus, hyperlipidemia and coronary artery disease. NAFLD represents a spectrum of liver diseases that include excessive accumulation of lipids in the hepatocytes, which is initially benign (hepatosteatosis) but progresses to a more advanced stage with inflammation (non-alcoholic steatohepatitis, NASH) and culminates in fibrosis accompanied by increased inflammation, apoptosis and scarring of liver tissue (cirrhosis). Patients with cirrhosis eventually progress to hepatocellular carcinoma (HCC). Therefore, patients with NAFLD and/or NASH have an increased risk of developing HCC later in life.

BRIEF SUMMARY

Compound 1, which has a chemical name of 2-(3,5-dichloro-4-((5-isopropyl-6-oxo-1,6-dihydropyridazin-3-yl)oxy)phenyl)-6-methyl-1,2,4-triazine-3,5(2H,4H)-dione), is useful for the treatment of a disease or disorder modulated by TR agonists such as a non-alcoholic fatty liver disease and/or NASH, see International Application No. PCT/CN2019/110494, filed Oct. 11, 2019, published as WO2020/073974, the content of which is incorporated herein by reference in its entirety.

In various embodiments, the present disclosure is directed to Compound 1, or its pharmaceutically acceptable salt, such as sodium salt or potassium salt, etc., for example, in a solid form.

Some embodiments of the present disclosure are directed to Compound 1 or its pharmaceutically acceptable salts in a crystalline form. For example, in some embodiments, Compound 1 can be in a crystalline Form I. In some embodiments, Compound 1 can be in a crystalline Form II. In some embodiments, the present disclosure provides a sodium salt of Compound 1. In some embodiments, the sodium salt of Compound 1 can be in a crystalline Form A. In some embodiments, the present disclosure provides a potassium salt of Compound 1. In some embodiments, the potassium salt of Compound 1 can be in a crystalline Form 1. In some embodiments, the potassium salt of Compound 1 can be in a crystalline Form 2. In any of the embodiments described herein, the Compound 1 or its pharmaceutically acceptable salt (e.g., sodium or potassium salt) can be substantially pure. The crystalline forms Form I, II, A, 1, and 2 are defined herein.

Certain embodiments of the present disclosure are directed to a pharmaceutical composition comprising one or more compounds of the present disclosure (e.g., Compound 1 in Form I or II, the sodium salt of Compound 1 in Form A, the potassium salt of Compound 1 in Form 1 or 2, an amorphous form of Compound 1, its sodium salt or potassium salt, or any combinations thereof). The pharmaceutical composition described herein can be formulated for different routes of administration, such as oral administration, parenteral administration, or inhalation etc.

Certain embodiments of the present disclosure are directed to a method of treating a disease or disorder associated with TR agonist, such as a non-alcoholic fatty liver disease. In some embodiments, the method comprises administering to the subject in need thereof a therapeutically effective amount of one or more compounds of the present disclosure (e.g., Compound 1 in Form I or II, the sodium salt of Compound 1 in Form A, the potassium salt of Compound 1 in Form 1 or 2, an amorphous form of Compound 1, its sodium salt or potassium salt, or any combinations thereof) or a pharmaceutical composition comprising the one or more compounds of the present disclosure as defined herein. In some embodiments, the administering comprises administration via oral administration, parenteral administration or inhalation. Non-limiting diseases or disorders suitable to be treated with the methods described herein include obesity, hyperlipidemia, hypercholesterolemia, diabetes, non-alcoholic steatohepatitis, fatty liver, non-alcoholic fatty liver disease, bone disease, thyroid axis alteration, atherosclerosis, a cardiovascular disorder, tachycardia, hyperkinetic behavior, hypothyroidism, goiter, attention deficit hyperactivity disorder, learning disabilities, mental retardation, hearing loss, delayed bone age, neurologic or psychiatric disease, thyroid cancer, and combinations thereof.

It is to be understood that both the foregoing summary and the following detailed description are exemplary and explanatory only, and are not restrictive of the invention herein.

BRIEF DESCRIPTION OF THE DRAWINGS/FIGURES

Figure 3A:
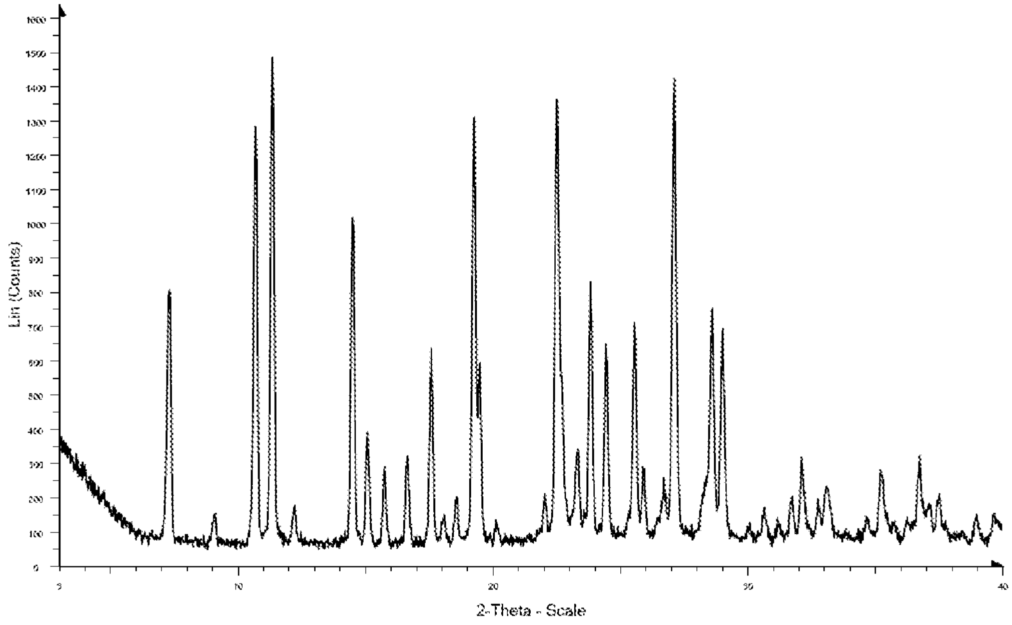
Figure 3B:
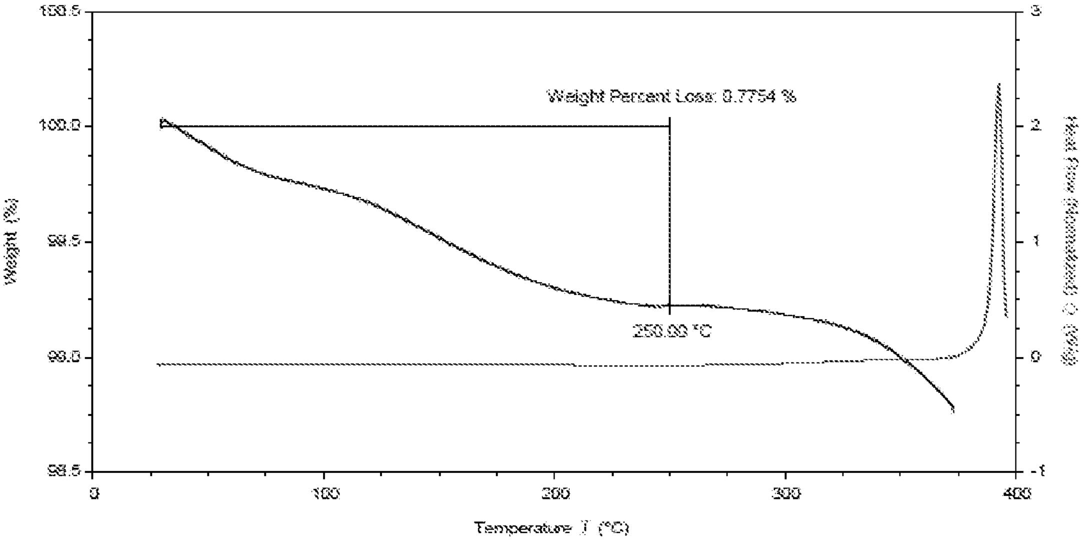
Figure 3C:
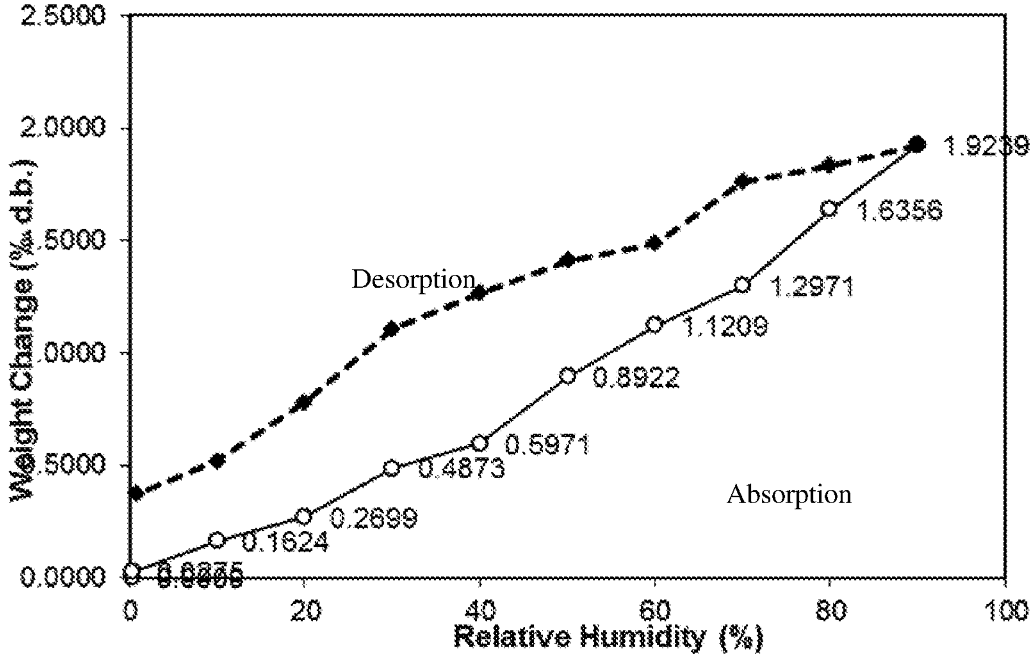

FIG. 3A shows a representative XRPD spectrum of crystalline Form A of the sodium salt of Compound 1. FIG. 3B shows representative TGA and DSC spectra of crystalline Form A of the sodium salt of Compound 1. FIG. 3C shows a representative DVS spectrum of crystalline Form A of the sodium salt of Compound 1.

Figure 4A:
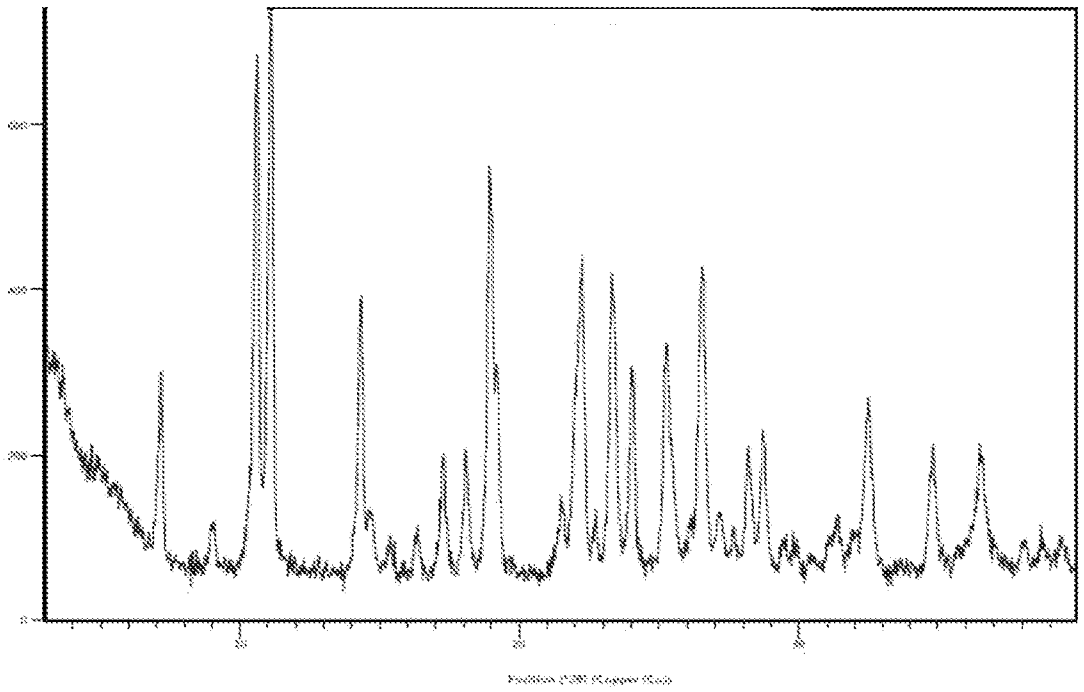
Figure 4B:
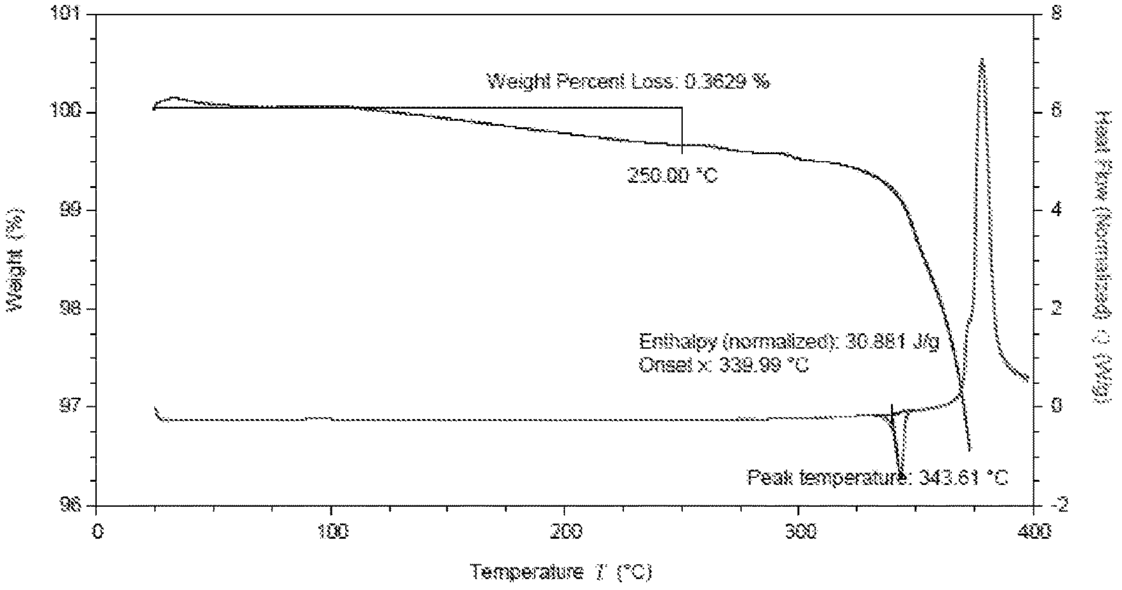
Figure 4C:
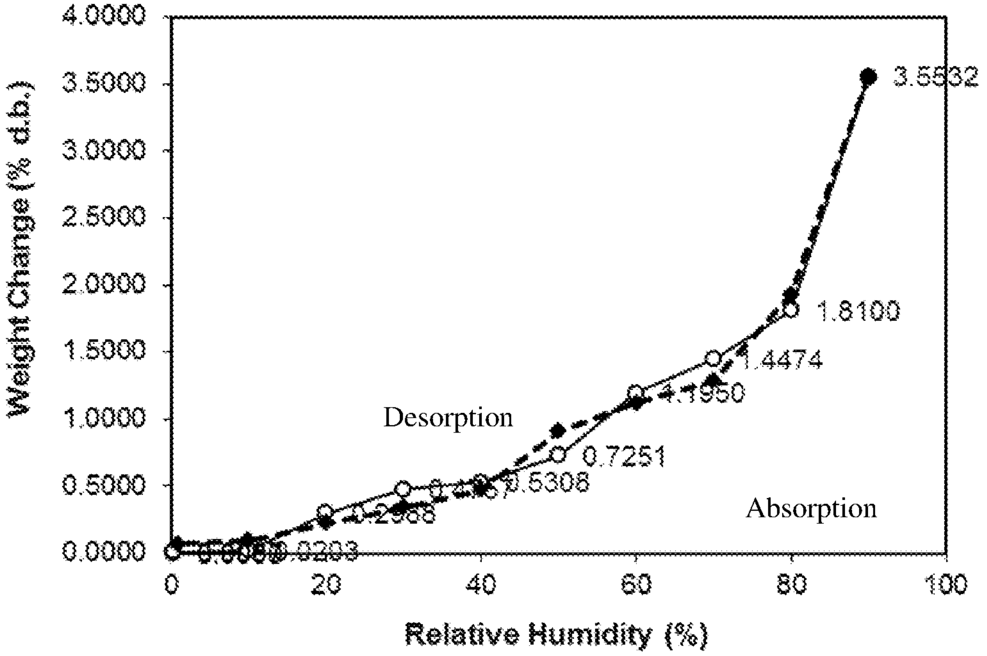

FIG. 4A shows a representative XRPD spectrum of crystalline Form 1 of the potassium salt of Compound 1. FIG. 4B shows representative TGA and DSC spectra of crystalline Form 1 of the potassium salt of Compound 1. FIG. 4C shows a representative DVS spectrum of crystalline Form 1 of the potassium salt of Compound 1.

Figure 5A:
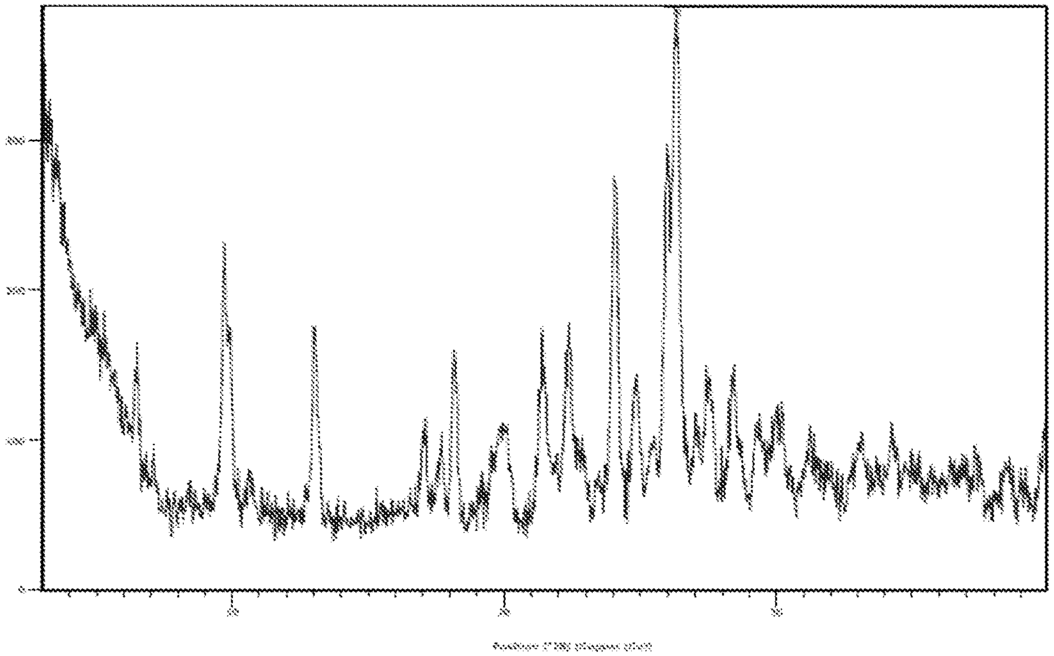
Figure 5B:
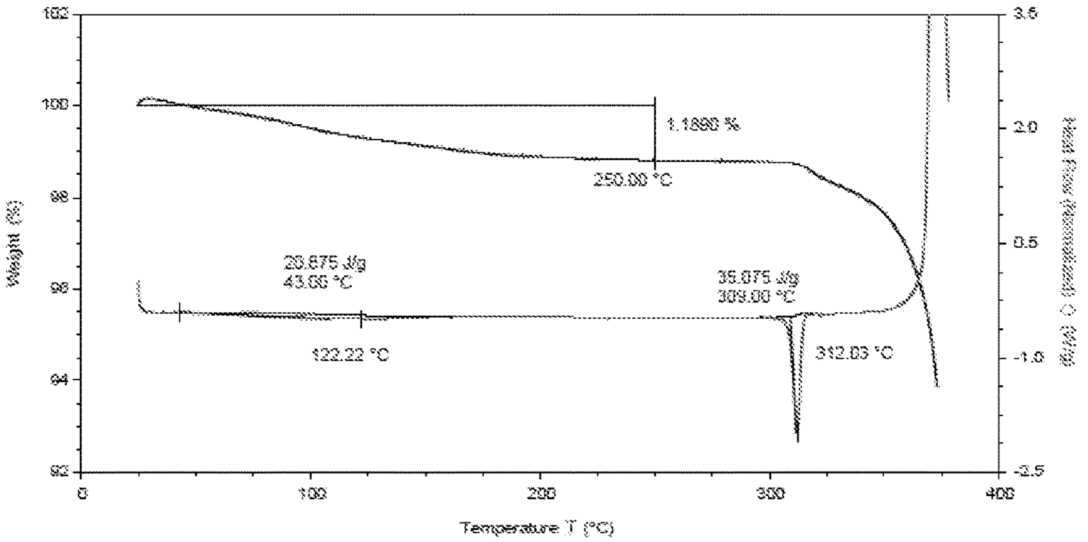
Figure 5C:
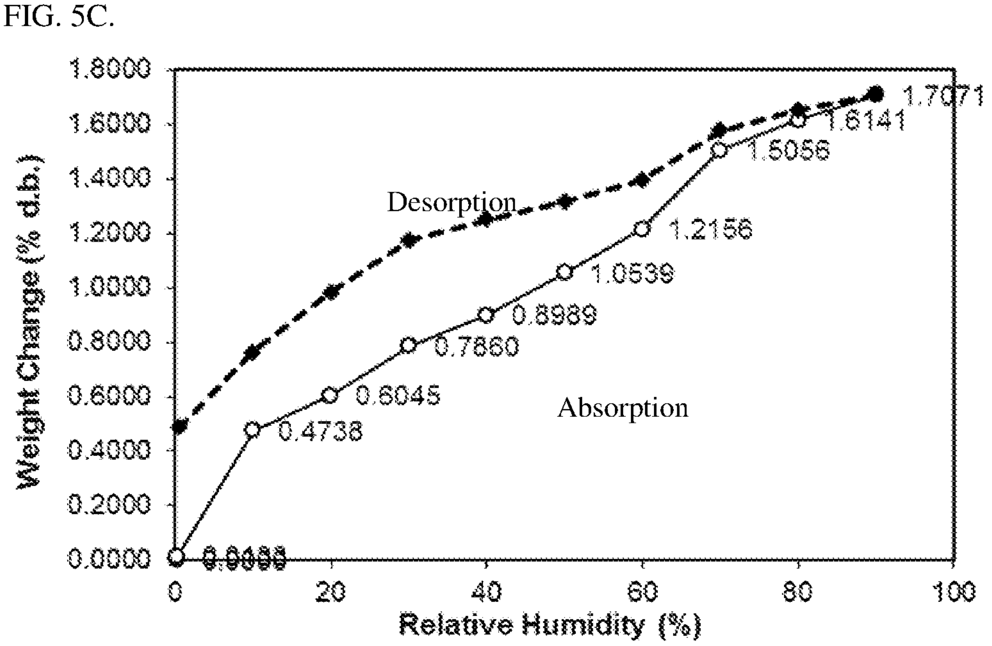

FIG. 5A shows a representative XRPD spectrum of crystalline Form 2 of the potassium salt of Compound 1. FIG. 5B shows representative TGA and DSC spectra of crystalline Form 2 of the potassium salt of Compound 1. FIG. 5C shows a representative DVS spectrum of crystalline Form 2 of the potassium salt of Compound 1.

Figure 6A:
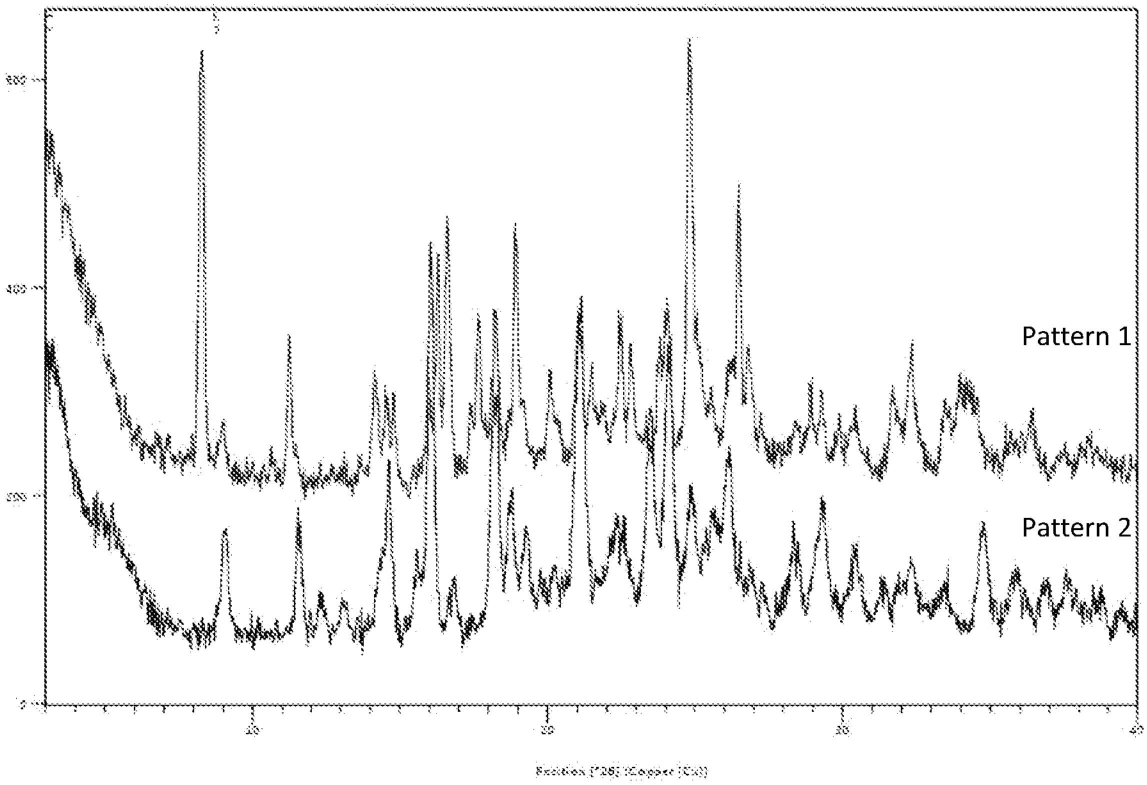
Figure 6B:
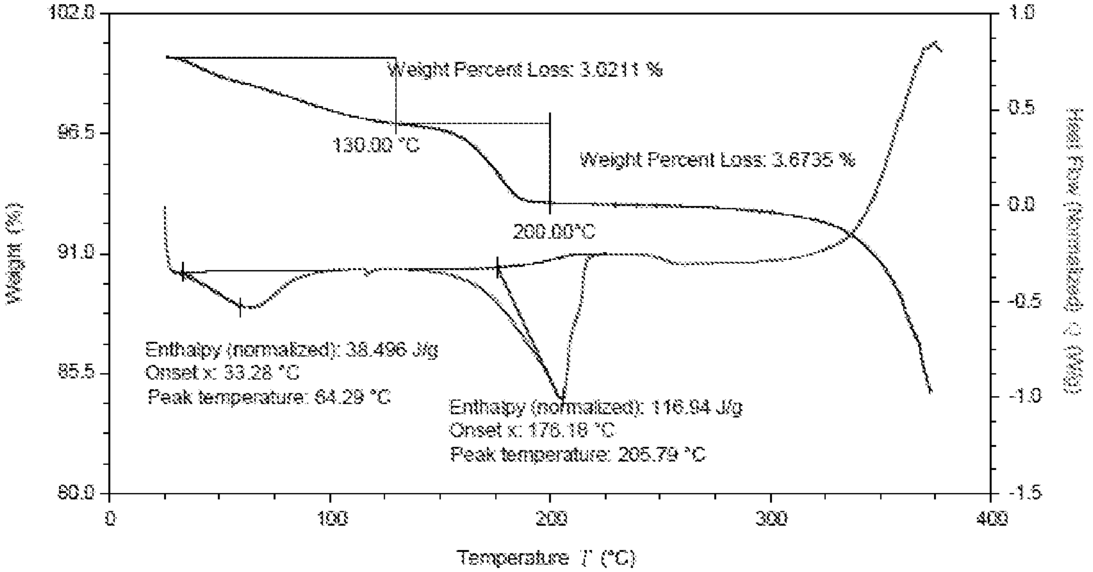
Figure 6C:
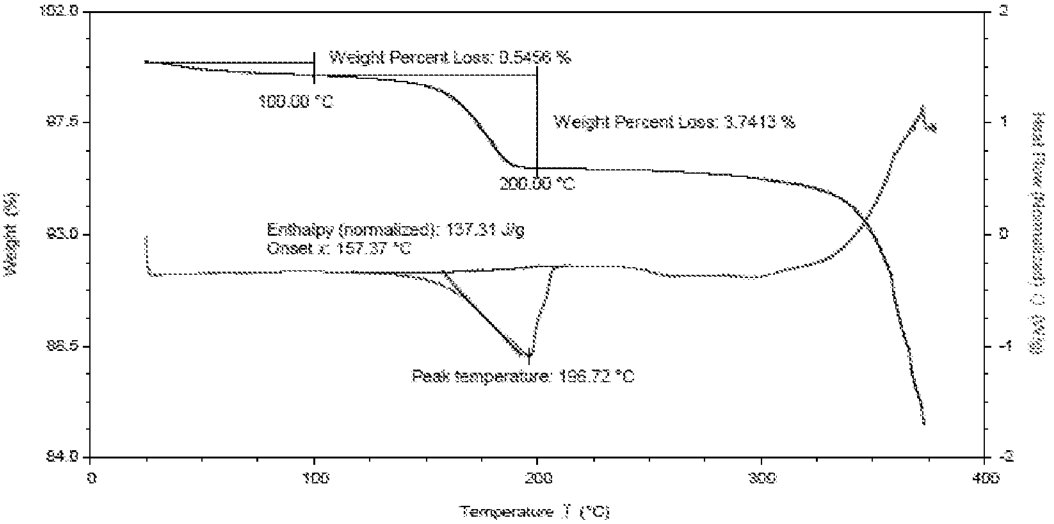
Figure 6D:
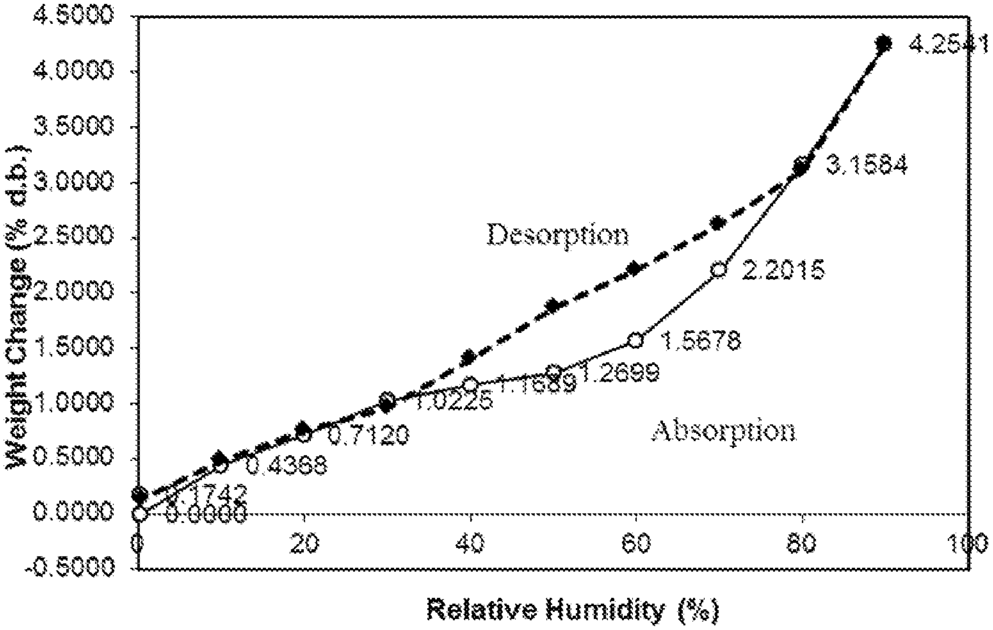

FIG. 6A shows a representative XRPD spectrum of crystalline Patterns 1 and 2 of the calcium salt of Compound 1. FIG. 6B shows representative TGA and DSC spectra of crystalline Pattern 1 of the calcium salt of Compound 1. FIG. 6C shows representative TGA and DSC spectra of crystalline Pattern 2 of the calcium salt of Compound 1. FIG. 6D shows a representative DVS spectrum of crystalline Pattern 2 of the calcium salt of Compound 1.

Figure 7A:
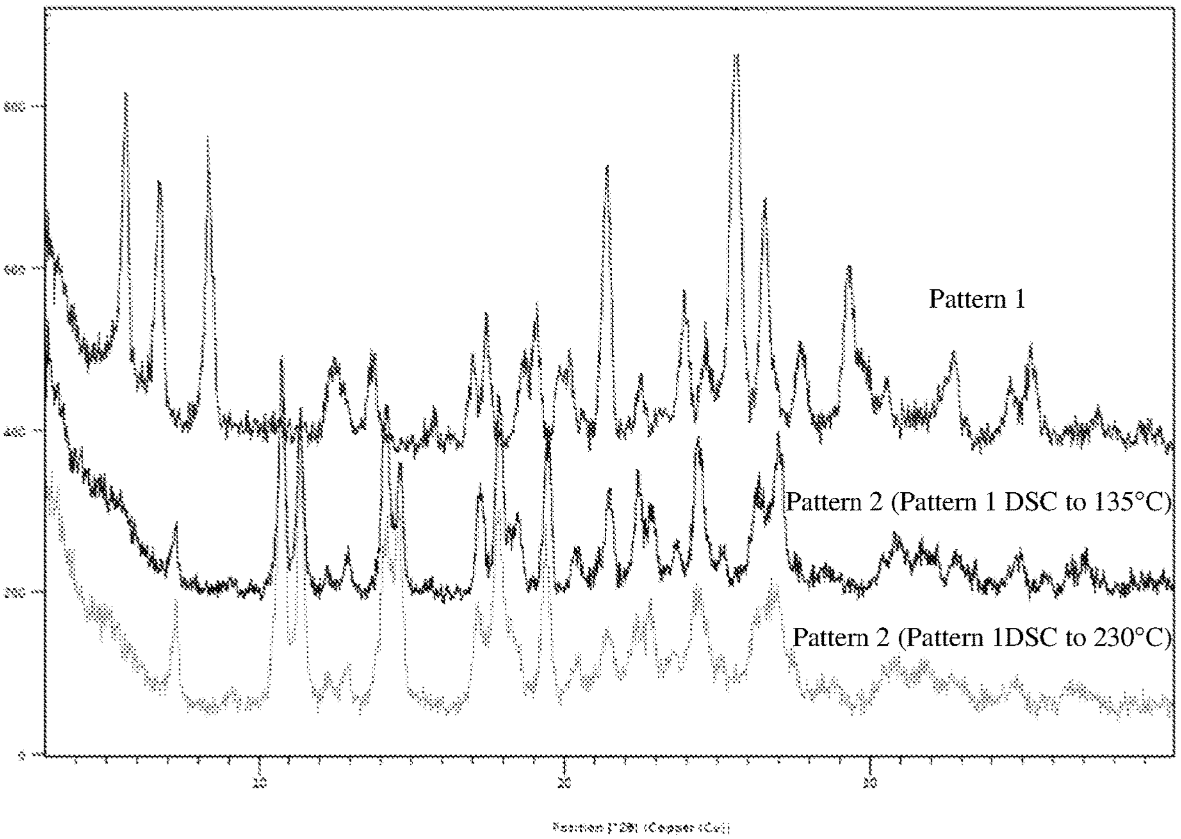
Figure 7B:
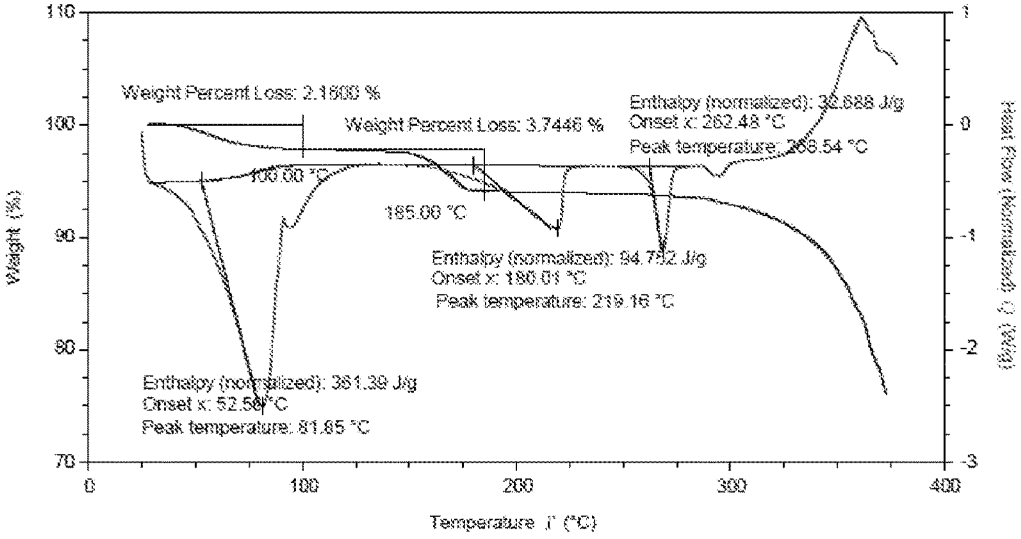

FIG. 7A shows a representative XRPD spectrum of crystalline Patterns 1 and 2 of the magnesium salt of Compound 1. FIG. 7B shows representative TGA and DSC spectra of crystalline Pattern 1 of the magnesium salt of Compound 1.

DETAILED DESCRIPTION

TR agonists have shown significant promise in the treatment of hypercholesterolemia, hepatic steatosis, and weight loss. However, these non-selective TR agonists have been associated with adverse action on heart, bone and cartilage. Therefore, more selective and specific agents targeting TH signaling pathways, based on improved mechanistic understanding, will be needed to effectively and selectively target metabolic diseases. Recent studies suggest that thyroid hormone analogues that are specific for TRβ have potential therapeutic benefit for metabolic conditions such as NAFLD and NASH. For example, MGL-3196 was reported to be a liver-targeted thyroid hormone receptor-beta agonist with certain selectivity over TR-alpha. MGL-3196 was also found to be useful for lowering lipid content in clinical trials. See e.g., *Atherosclerosis* 230: 373-380 (2013).

International Application No. PCT/CN2019/110494, filed Oct. 11, 2019, published as WO2020/073974, the content of which is incorporated herein by reference in its entirety, describes Compound 1 as having high TR beta potency and selectivity over TR alpha and are useful for treating various diseases or disorders, such as NAFLD and NASH.

In various embodiments, the present disclosure provides Compound 1 as well as its pharmaceutically acceptable salts such as sodium or potassium salt, for example, in an isolated form, a substantially pure form, and/or in a solid form including crystalline forms and/or amorphous forms. Also provided are methods of preparing the Compound 1 and its pharmaceutically acceptable salts as well as methods of using the same, for example, in treating or preventing a disease or disorder described herein, such as NAFLD and NASH.

Compound 1

In some embodiments, the present disclosure is directed to Compound 1, which is represented by the formula below:

1

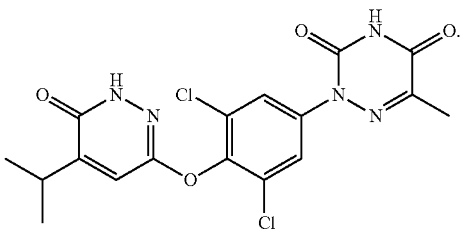

Compound 1 has a chemical name of 2-(3,5-dichloro-4-((5-isopropyl-6-oxo-1,6-dihydropyridazin-3-yl)oxy)phenyl)-6-methyl-1,2,4-triazine-3,5(2H,4H)-dione, based on ChemDraw software v. 18.0. One measurement showed that Compound 1 has a pKa of about 6.5 and about 10.5 in water. When forming a salt described herein, those skilled in the art would understand that the hydrogen of the N—H of the triazinedione ring would be deprotonated to form an anion, which can be represented by the following structure:

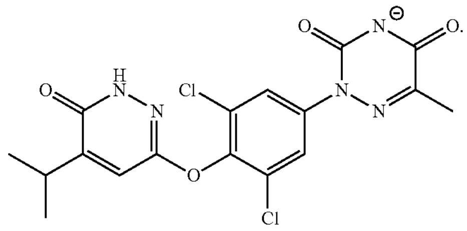

1-anion

The molar ratio of the anion (1-aninon) to the cation of a salt can vary depending on the nature of the cation so that the salt is electrically neutral or charge balanced. For example, for salts having monovalent cations herein, such as sodium or potassium salt, the molar ratio of the monovalent cations (e.g., $Na^+$, $K^+$, etc.) to the anion 1-anion is about 1:1. For salts having divalent cations herein, such as calcium or magnesium salt, the molar ratio of the divalent cations (e.g., $Ca^{2+}$, $Mg^{2+}$, etc.) to the anion 1-anion can be about 1:1 or 1:2, and when the ratio is about 1:1, the salt also contains an additional anion such that the salt is electrically neutral or charge balanced.

Compound 1 can be in a solid form, such as an amorphous form, a crystalline form, or a combination thereof. In some embodiments, Compound 1 can be in an amorphous form.

In some embodiments, the present disclosure provides Compound 1 in a crystalline form (e.g., Form I or II as described herein). As used herein, when a compound or salt (e.g., Compound 1) is said to exist or be in one particular solid form (e.g., a crystalline form), it should be understood that in some embodiments, the compound or salt can exist predominantly in that particular form. However, in some embodiments, the compound or salt can also exist in the particular form, in a mixture with one or more other solid forms, including amorphous form. For example, when Compound 1 is said to exist or be in Form I, Compound 1 can exist predominantly in Form I, such as more than 80% by weight, more than 90% by weight, or more than 95% by weight of Compound 1 are in Form I, or no other solid form can be identified, for example, by XRPD; or in some embodiments, Compound 1 can exist in Form I, in a mixture with one or more solid forms such as an amorphous form.

Figure 1A:
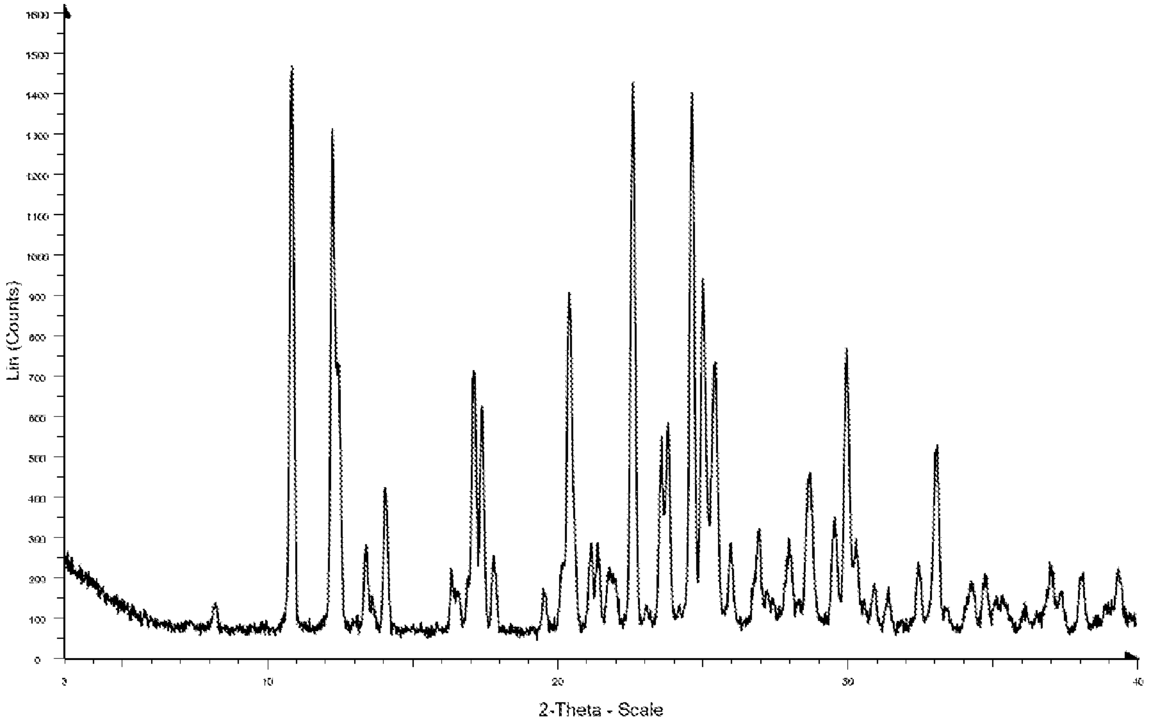
FIG. 1A shows a representative X-ray powder diffraction (XRPD) spectrum of crystalline Form I of Compound 1.
Figure 1B:
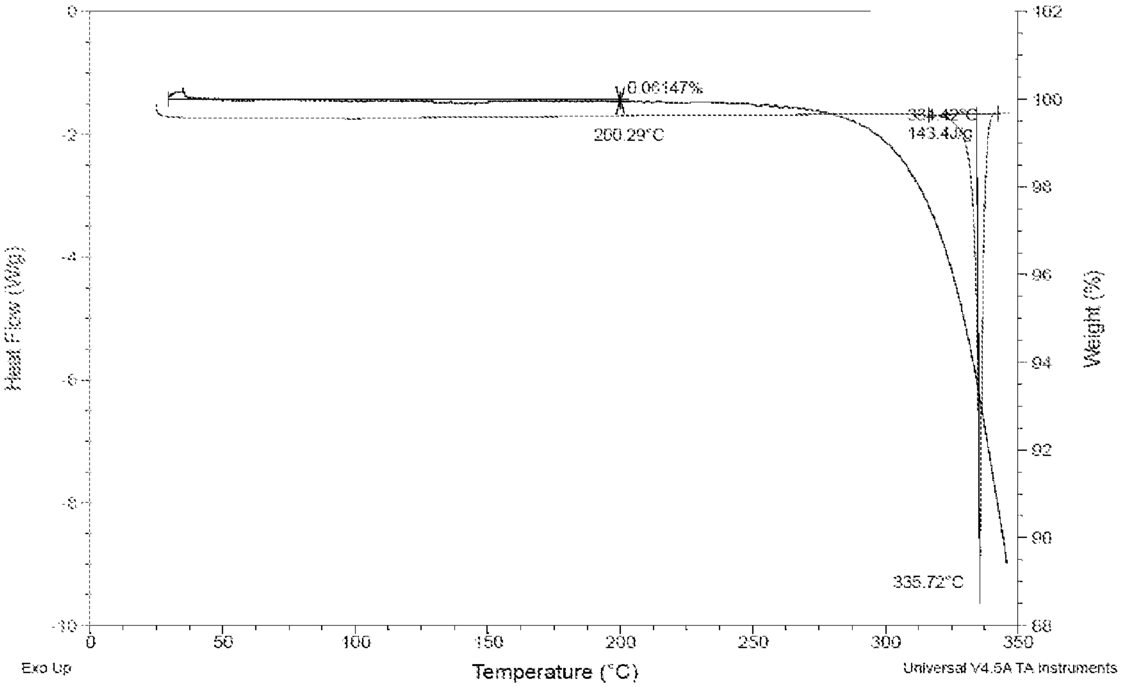
FIG. 1B shows representative thermogravimetric analysis (TGA) and differential scanning calorimetry (DSC) spectra of crystalline Form I of Compound 1.

In some embodiments, Compound 1 is in a crystalline Form I. Characteristics of Form I include any of those described herein. In some embodiments, crystalline Form I can be characterized by (1) an X-ray powder diffraction (XRPD) pattern having one or more (e.g., 2, 4, 6, 8, 10, or 12) of the following peaks: 10.8, 12.2, 12.4, 14.0, 17.1, 17.8, 22.6, 23.6, 24.6, 25.4, 26.0, and 28.8, degrees 2 theta, ±0.2°; (2) an X-ray powder diffraction (XRPD) pattern having one or more (e.g., 2, 4, 6, 8, 10, 12, or all) of the following peaks: 10.8, 12.2, 12.4, 14.0, 17.1, 17.4, 17.8, 20.1, 20.4, 22.6, 23.6, 24.6, 25.0, 25.4, 26.0, 28.8, 30.0, and 33.1 degrees 2 theta, ±0.2°; (3) an XRPD pattern substantially the same as shown in FIG. 1A or Table 1; (4) a Differential Scanning calorimetry (DSC) pattern substantially the same as shown in FIG. 1B; or any combination thereof (e.g., (1) and (4), (2) and (4), (1), (2) and (4), or (3) and (4)). In some embodiments, the crystalline Form I can be characterized by an XRPD pattern having the major peaks (e.g., peaks with relative intensity of 20% or above, 30% or above, 40% or above, 50% or above, 60% or above, 70% or above, 80% or above, or 90% or above) of FIG. 1A or as shown in Table 1, degrees 2 theta, ±0.2°. To be clear, when it is said that the XRPD pattern of Form I has the major peaks of FIG. 1A or Table 1 or is substantially the same as FIG. 1A, it does not require that the XRPD pattern have the same relative intensities for the corresponding peaks as shown in FIG. 1A or Table 1, as applicable. It suffices that the XRPD pattern includes the peaks at the respective diffraction angels (degrees 2 theta, ±0.2°) corresponding to the peaks as shown in FIG. 1A or Table 1, as applicable, regardless of their relative intensities. Similar expressions as to other crystalline forms herein should be understood similarly. In some embodiments, the crystalline Form I can be characterized by an XRPD pattern having all of the following peaks: 10.8, 12.2, 12.4, 14.0, 17.1, 17.8, 22.6, 23.6, 24.6, 25.4, 26.0, and 28.8, degrees 2 theta, ±0.2°. In some embodiments, the crystalline Form I can also be characterized by a DSC pattern having an endothermic peak with an onset temperature of about 334.4° C. and/or peak temperature at about 335.7° C. As shown in the Examples section, Form I was determined to be an anhydrate. In some embodiments, the crystalline Form I is substantially the same as the crystalline Form I obtained in Example 2 of this application.

The Compound 1 in crystalline Form I can be prepared by methods described herein. For example, in some embodiments, Compound 1 in crystalline Form I can be prepared by a method comprising 1) reacting compound 1-7 with water, e.g., in acetic acid in the presence of a base (e.g., potassium acetate), under heat, such as at refluxing temperature of acetic acid; 2) cooling the mixture to provide a crude solid; and 3) slurrying the crude solid in dimethyl sulfoxide (DMSO) and water to obtain crystalline Form I. In some embodiments, Compound 1 in crystalline Form I can be obtained by a method comprising 1) dissolving Compound 1 in DMSO to form a solution; and then 2) adding an anti-solvent, such as MeOH, ethyl acetate (EA), acetonitrile (ACN), isopropyl acetate (IPAC), EtOH, methyl ethyl ketone or 2-butanone (MEK), Water, Acetone, isopropyl alcohol (IPA), tetrahydrofuran (THF), Toluene, or n-Butanol to the solution to precipitate Compound 1 in crystalline Form I. In some embodiments, Compound 1 in crystalline Form I can be obtained by a method comprising 1) dissolving Compound 1 in DMSO to form a solution; and then 2) adding the solution to an anti-solvent, such as MeOH, EA, ACN, EtOH, MEK, Water, Acetone, IPA, THF, Toluene, or n-Butanol to precipitate Compound 1 in crystalline Form I. Exemplified procedures for preparing Compound 1 in Form I are shown in Examples 2 and 3 of this application.

Figure 2A:
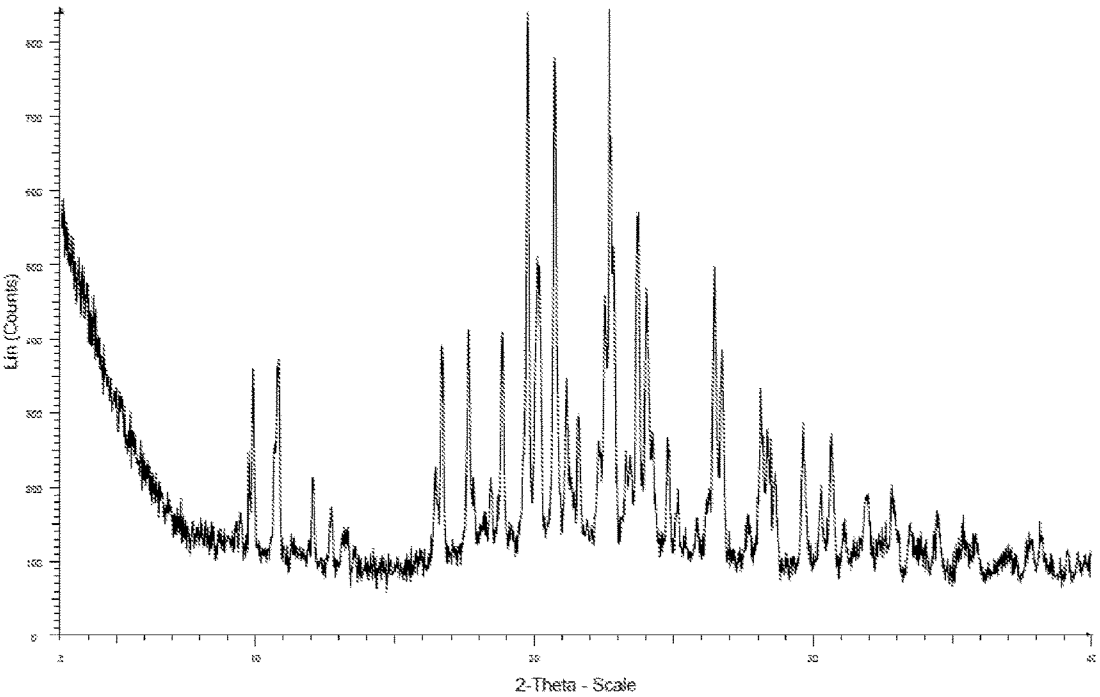
FIG. 2A shows a representative XRPD spectrum of crystalline Form II of Compound 1.
Figure 2B:
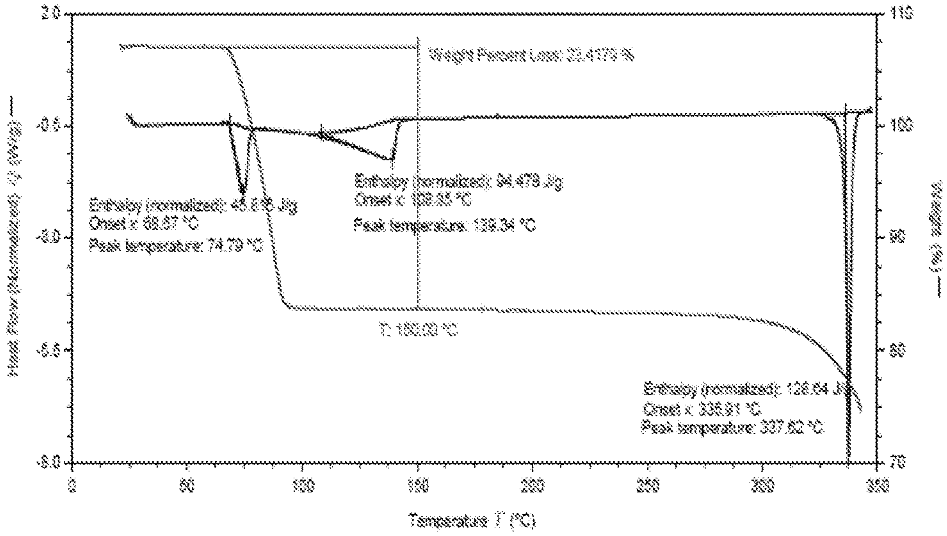
FIG. 2B shows representative TGA and DSC spectra of crystalline Form II of Compound 1.

In some embodiments, Compound 1 is in a crystalline Form II. Characteristics of Form II include any of those described herein. In some embodiments, crystalline Form II can be characterized by (1) an X-ray powder diffraction (XRPD) pattern having one or more (e.g., 2, 4, 6, 8, 10, or all) of the following peaks: 16.7, 17.6, 18.9, 19.8, 20.1, 20.7, 22.5, 22.7, 23.7, 24.0, and 26.5, degrees 2 theta, ±0.2°; (2) an X-ray powder diffraction (XRPD) pattern having one or more (e.g., 2, 4, 6, 8, 10, 12, 16, 20, or all) of the following peaks: 9.9, 10.8, 16.7, 17.6, 18.9, 19.8, 20.1, 20.7, 21.2, 21.6, 22.3, 22.5, 22.7, 23.7, 24.0, 24.8, 26.5, 26.7, 28.1, 29.7, and 30.7, degrees 2 theta, ±0.2°; (3) an XRPD pattern substantially the same as shown in FIG. 2A or Table 2; (4) a Differential Scanning calorimetry (DSC) pattern substantially the same as shown in FIG. 2B; or any combination thereof (e.g., (1) and (4), (2) and (4), (1), (2) and (4), or (3) and (4)). In some embodiments, the crystalline Form II can be characterized by an XRPD pattern having the major peaks (e.g., peaks with relative intensity of 20% or above, 30% or above, 40% or above, 50% or above, 60% or above, 70% or above, 80% or above, or 90% or above) of FIG. 2A or as shown in Table 2, degrees 2 theta, ±0.2°. In some embodiments, the crystalline Form II can be characterized by an XRPD pattern having all of the following peaks: 16.7, 17.6, 18.9, 19.8, 20.1, 20.7, 22.5, 22.7, 23.7, 24.0, and 26.5, degrees 2 theta, ±0.2°. In some embodiments, the crystalline Form II can also be characterized by a DSC pattern having 1) a broad endothermic peak with an onset temperature of about 68.7° C. and/or peak temperature at about 74.8° C.; 2) a broad endothermic peak with an onset temperature of about 108.4° C. and/or peak temperature at about 139.3° C.; and 3) an endothermic peak with an onset temperature of about 335.9° C. and/or peak temperature at about 337.6° C. As shown in the Examples section, Form II was determined to be a DMSO solvate, with the molar ratio of DMSO to Compound 1 of about 1.5:1, based on the weight loss observed by TGA. In some embodiments, the crystalline Form II is substantially the same as the crystalline Form II obtained in Example 2 of this application. Form II can be converted into Form I through heating or slurrying in various solvent, such as in methanol, acetonitrile, acetone, ethyl acetate, water, etc.

The Compound 1 in crystalline Form II can be prepared by methods described herein. For example, in some embodiments, Compound 1 in crystalline Form II can be prepared by a method comprising 1) dissolving Compound 1 in DMSO to form a solution; and then 2) adding an anti-solvent, such as MTBE to the solution to precipitate Compound 1 in crystalline Form II. In some embodiments, Compound 1 in crystalline Form II can be obtained by a method comprising 1) dissolving Compound 1 in DMSO to form a solution; and then 2) adding the solution to an anti-solvent, such as methyl tert-Butyl ether (MTBE) or IPAC to precipitate Compound 1 in crystalline Form II. In some embodiments, Compound 1 in crystalline Form II can be obtained by a method comprising 1) heating Compound 1 in Form I in DMSO and a solvent selected from IPAC, MTBE, and toluene to form a mixture; and 2) then gradually cooling the mixture to form Compound 1 in crystalline Form II. In some embodiments, Compound 1 in crystalline Form II can be obtained by a method comprising 1) heating Compound 1 in Form I in DMSO and a solvent selected from MTBE and water to form a mixture; and 2) then quickly cooling the mixture to form Compound 1 in crystalline Form II. Exemplified procedures for preparing Compound 1 in Form II are shown in Example 3 of this application.

In some embodiments, Compound 1 can be in an amorphous form.

In some embodiments, the present disclosure also provides a solid form of Compound 1 that can be produced by any of the applicable methods described in the Examples section.

Compound 1 herein is typically in a substantially pure form. For example, in some embodiments, Compound 1 can have a purity of greater than 70%, preferably greater than 90% (e.g., greater than 95%, greater than 97%), by weight, by HPLC area, or both. In some embodiments, the Compound 1 can be characterized by a purity by weight and/or by HPLC area of about 70%, about 75%, about 80%, about 85%, about 90%, about 95%, about 97%, about 99%, or any ranges between the specified values. For example, in some embodiments, the Compound 1 can be characterized by a purity by HPLC area of about 70%, about 75%, about 80%, about 85%, about 90%, about 95%, about 97%, about 99%, or any ranges between the specified values. The substantially pure Compound 1 can be in a solid form (e.g., a crystalline form described herein, amorphous form, or a combination thereof) or in a solution, suspension, or another form. In some embodiments, the substantially pure Compound 1 can be in crystalline Form I. In some embodiments, the substantially pure Compound 1 can be in crystalline Form II. For the avoidance of doubt, a composition comprising the substantially pure Compound 1 herein and one or more other ingredients should be understood as a mixture of the substantially pure Compound 1 herein and the one or more other ingredients, for example, such composition can be obtained directly or indirectly from mixing the substantially pure Compound 1 with the one or more other ingredients, such as solvent, pharmaceutically acceptable excipients, etc. Similar expressions relating to compositions comprising the substantially pure salts of Compound 1 herein should be understood similarly. HPLC methods for determining purity of Compound 1 or its pharmaceutically acceptable salt such as the sodium or potassium salt herein can be readily determined by those skilled in the art in view of the present disclosure. Exemplary HPLC methods for purity determination are also shown in the Examples section.

Compound 1 herein can be used for preparing a pharmaceutical composition herein. For example, in some embodiments, the pharmaceutical composition can be prepared by mixing Compound 1 (e.g., Form I or II, or in combination with an amorphous form) with a pharmaceutically acceptable excipient.

In some embodiments, Compound 1 herein can also be used as a "starting material" for the preparation of a salt herein, such as a sodium salt or potassium salt, which is used for the preparation of a pharmaceutical composition. As discussed in detail herein, the sodium or potassium salt has a much improved purity and solubility compared to Compound 1 itself and can be more suited for pharmaceutical developments.

Sodium Salt of Compound 1

In some embodiments, the present disclosure is directed to a sodium salt of Compound 1. The sodium salt can be readily obtained by treating Compound 1 with a sodium base such as sodium hydroxide, sodium methoxide, etc. The molar ratio of sodium to Compound 1 of the sodium salt herein is typically about 1:1. For example, the sodium salt herein can be represented by the following formula:

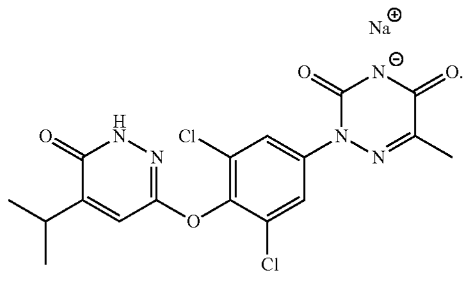

1-Na

The sodium salt of Compound 1 can be in a solid form, such as an amorphous form, a crystalline form, or a combination thereof. For example, in some embodiments, the sodium salt of Compound 1 can be an amorphous form.

In some embodiments, the sodium salt of Compound 1 is in a crystalline Form A. Characteristics of Form A of the sodium salt of Compound 1 include any of those described herein. In some embodiments, crystalline Form A can be characterized by (1) an X-ray powder diffraction (XRPD) pattern having one or more (e.g., 2, 4, 6, 8, or 10) of the following peaks: 7.3, 10.7, 11.3, 14.5, 19.2, 22.5, 23.8, 25.6, 27.1, and 28.6, degrees 2 theta, ±0.2°; (2) an X-ray powder diffraction (XRPD) pattern having one or more (e.g., 2, 4, 6, 8, 10, 12, 14, 16, or all) of the following peaks: 7.3, 10.7, 11.3, 14.5, 15.0, 15.7, 16.6, 17.5, 19.2, 19.5, 22.5, 23.3, 23.8, 24.4, 25.6, 27.1, 28.6, 29.0, 32.1, 35.2 and 36.8, degrees 2 theta, ±0.2°; (3) an XRPD pattern substantially the same as shown in FIG. 3A or Table 3; (4) a Differential Scanning calorimetry (DSC) pattern substantially the same as shown in FIG. 3B; or any combination thereof (e.g., (1) and (4), (2) and (4), (1), (2) and (4), or (3) and (4)). In some embodiments, the crystalline Form A can be characterized by an XRPD pattern having the major peaks (e.g., peaks with relative intensity of 20% or above, 30% or above, 40% or above, 50% or above, 60% or above, 70% or above, 80% or above, or 90% or above) of FIG. 3A or as shown in Table 3, degrees 2 theta, ±0.2°. In some embodiments, the crystalline Form A can be characterized by an XRPD pattern having all of the following peaks: 7.3, 10.7, 11.3, 14.5, 19.2, 22.5, 23.8, 25.6, 27.1, and 28.6, degrees 2 theta, ±0.2°. In some embodiments, the crystalline Form A can also be characterized by a DSC pattern having no endothermic peak up to 380° C. As shown in the Examples section, Form A was determined to be an anhydrate. In some embodiments, the crystalline Form A is substantially the same as the crystalline Form A obtained in Example 4 of this application.

The sodium salt of Compound 1 in crystalline Form A can be prepared by methods described herein. For example, in some embodiments, the sodium salt of Compound 1 in crystalline Form A can be prepared by a method comprising 1) mixing Compound 1 with a sodium base, e.g., aqueous or solid sodium hydroxide, in a solvent (e.g., methanol) to form a suspension or solution, typically under heat, such as about 50° C.; and 2) cooling the suspension or solution to provide crystalline Form A. The sodium base is typically used in slightly excess, such as at about 1.1 to about 1.5 molar equivalent of Compound 1. The suspension or solution is typically stirred for a period of time under heat, such as about 50° C. before the cooling step. In some embodiments, an antisolvent can also be added. For example, crystalline Form A can be obtained by any of the following procedures:

- Add Compound 1 into NaOH-MeOH solution. The Suspension was stirred for 2 hours at RT and then filtered.
- Compound 1 was suspended in 10V MeOH at 60° C., then NaOH was added. 6V DMSO was added and kept stirring for 60 min, then cooled to RT. 18V Acetone was added and the suspension was kept stirring overnight.
- Compound 1 was added into 10V DMSO at 50° C. and stirred for 10 min. Solid partly dissolved. NaOH was added and the suspension was stirred at 50° C. for 20 min. 2V water was added and solid dissolved completely after stirring for 20 min. 24V acetone, 120V EA and 24V MeOH were added step by step. The mixture was kept stirring overnight and solid was collected by filtration.
- Compound 1 was suspended in 4V DMSO at 50° C. Then NaOH aqueous was added. Solid dissolved completely. Solid precipitated rapidly. The suspension was stirred at 50° C. for 5 min. 10V MeOH and 20V acetone were added and the mixture was stirred for 10 min. Then cooled to RT and stirred for 30 min.
- Compound 1 was suspended in 10V MeOH, then NaOH aqueous was added. The suspension was kept stirring at 50° C. overnight.
- Compound 1 was suspended 15V MeOH, the mixture was stirred at 50° C. for 10 min. Then NaOH aqueous was added. The suspension was kept stirring for 3 hours and then cooled to RT with stirring for 1 hour.

Exemplified representative procedures for preparing sodium salt of Compound 1 in crystalline Form A are shown in Example 4 of this application.

In some embodiments, the sodium salt of Compound 1 can be in an amorphous form.

In some embodiments, the present disclosure also provides a solid form of the sodium salt of Compound 1 that can be produced by any of the applicable methods described in the Examples section.

The sodium salt of Compound 1 herein is typically in a substantially pure form. For example, in some embodiments, the sodium salt of Compound 1 can have a purity of greater than 70%, preferably greater than 90% (e.g., greater than 95%, greater than 97%, greater than 98%), by weight, by HPLC area, or both. In some embodiments, the sodium salt of Compound 1 can be characterized by a purity by weight and/or by HPLC area of about 70%, about 75%, about 80%, about 85%, about 90%, about 95%, about 97%, about 99%, or any ranges between the specified values. For example, in some embodiments, the sodium salt of Compound 1 can be characterized by a purity by HPLC area of about 70%, about 75%, about 80%, about 85%, about 90%, about 95%, about 97%, about 99%, or any ranges between the specified values. The substantially pure the sodium salt of Compound 1 can be in a solid form (e.g., a crystalline form described herein, amorphous form, or a combination thereof) or in a solution, suspension, or another form. In some embodiments, the substantially pure the sodium salt of Compound 1 can be in crystalline Form A.

The substantially pure sodium salt of Compound 1 herein typically has a sodium content close to the theoretical sodium content calculated based on a molar ratio of sodium to Compound 1 of 1:1. In some embodiments, the substantially pure sodium salt of Compound 1 is characterized by a molar ratio of sodium to Compound 1 of about 1:1. In some embodiments, the substantially pure sodium salt of Compound 1 has a sodium content of about 80% to about 125% of the theoretical sodium content. Sodium content can be determined by known methods, such as by ion chromatography.

The substantially pure sodium salt of Compound 1 herein can be free or substantially free of Compound 1 (free acid), and/or can be free or substantially free of other salts of Compound 1. In some embodiments, the substantially pure sodium salt of Compound 1 is substantially free of Compound 1, for example, with an amount of less than 5% by weight (e.g., less than 3%, less than 1%, less than 0.2%, less than 0.1% or less than 0.05%). In some embodiments, the substantially pure sodium salt of Compound 1 is free of Compound 1, other than an amount that may exist through equilibrium. In some embodiments, the substantially pure sodium salt of Compound 1 has no detectable amount of Compound 1. In some embodiments, the substantially pure sodium salt of Compound 1 is substantially free of other salts of Compound 1, for example, with an amount less than 5% by weight (e.g., less than 3%, less than 1%, less than 0.2%, less than 0.1% or less than 0.05%). In some embodiments, the substantially pure sodium salt of Compound 1 includes no detectable amount of other salts of Compound 1.

Potassium Salt of Compound 1

In some embodiments, the present disclosure is directed to a potassium salt of Compound 1. The potassium salt can be readily obtained by treating Compound 1 with a potassium base such as potassium hydroxide, potassium methoxide, etc. The molar ratio of potassium to Compound 1 of the potassium salt herein is typically about 1:1. For example, the potassium salt herein can be represented by the following formula:

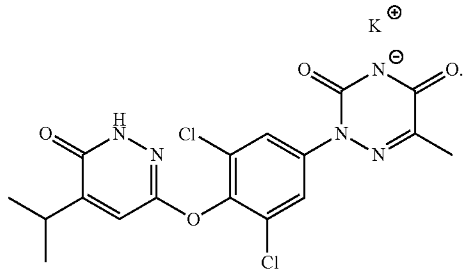

1-K

The potassium salt of Compound 1 can be in a solid form, such as an amorphous form, a crystalline form, or a combination thereof. For example, in some embodiments, the sodium salt of Compound 1 can be an amorphous form.

In some embodiments, the potassium salt of Compound 1 is in a crystalline Form 1. Characteristics of Form 1 of the potassium salt of Compound 1 include any of those described herein. In some embodiments, crystalline Form 1 can be characterized by (1) an X-ray powder diffraction (XRPD) pattern having one or more (e.g., 2, 4, 6, or all) of the following peaks: 10.6, 11.1, 14.3, 18.9, 22.3, 23.3, and 26.6, degrees 2 theta, ±0.2°; (2) an X-ray powder diffraction (XRPD) pattern having one or more (e.g., 2, 4, 6, 8, 10, 12, 14, 16, or all) of the following peaks: 7.2, 10.6, 11.1, 14.3, 17.2, 18.1, 18.9, 22.3, 23.3, 24.0, 25.2, 26.6, 28.2, 28.7, 32.5, 34.8, and 36.5, degrees 2 theta, ±0.2°; (3) an XRPD pattern substantially the same as shown in FIG. 4A or Table 4; (4) a Differential Scanning calorimetry (DSC) pattern substantially the same as shown in FIG. 4B; or any combination thereof (e.g., (1) and (4), (2) and (4), (1), (2) and (4), or (3) and (4)). In some embodiments, the crystalline Form 1 can be characterized by an XRPD pattern having the major peaks (e.g., peaks with relative intensity of 20% or above, 30% or above, 40% or above, 50% or above, 60% or above, 70% or above, 80% or above, or 90% or above) of FIG. 4A or as shown in Table 4, degrees 2 theta, ±0.2°. In some embodiments, the crystalline Form 1 can be characterized by an XRPD pattern having all of the following peaks: 10.6, 11.1, 14.3, 18.9, 22.2, 23.3, and 26.6, degrees 2 theta, ±0.2°. In some embodiments, the crystalline Form 1 can also be characterized by a DSC pattern having an endothermic peak with an onset temperature of about 340.0° C. and/or a peak temperature of about 343.6° C. As shown in the Examples section, Form 1 was determined to be an anhydrate. In some embodiments, the crystalline Form 1 is substantially the same as the crystalline Form 1 obtained in Example 5 of this application.

The potassium salt of Compound 1 in crystalline Form 1 can be prepared by methods described herein. For example, in some embodiments, the potassium salt of Compound 1 in crystalline Form 1 can be prepared by a method comprising 1) mixing Compound 1 with a potassium base, e.g., solid potassium hydroxide, in a non-aqueous solvent (e.g., methanol) to form a suspension or solution, typically under heat, such as about 50° C.; and 2) cooling the suspension or solution to provide crystalline Form 1. As discussed herein, the potassium salt prepared in a solvent containing water typically results in crystalline Form 2 (described below). Thus, the method of preparation of Form 1 typically controls the reaction system to have a minimal presence of water, for example, the solvent system typically should have a water content of less than 0.5% volume/volume. Similarly, the potassium base added typically is not an aqueous solution. For example, the potassium base can be added in a solid form or dissolved or suspended in an organic solvent. The potassium base is typically used in slightly excess, such as at about 1.1 to about 1.5 molar equivalent of Compound 1. The suspension or solution is typically stirred for a period of time under heat, such as about 50° C. before the cooling step. In some embodiments, an antisolvent such as ethyl acetate can also be added. In some embodiments, the potassium salt of Compound 1 in crystalline Form 1 can also be prepared from Form 2, for example, by stirring Form 2 in a solvent system that has water content of less than 0.5% volume/volume. Exemplified representative procedures for preparing potassium salt of Compound 1 in crystalline Form 1 are shown in Examples 5, 7 and 10 of this application.

In some embodiments, the potassium salt of Compound 1 is in a crystalline Form 2. Characteristics of Form 2 of the potassium salt of Compound 1 include any of those described herein. In some embodiments, crystalline Form 2 can be characterized by (1) an X-ray powder diffraction (XRPD) pattern having one or more (e.g., 2, 4, or all) of the following peaks: 9.7, 13.0, 24.1, 26.0, and 26.3, degrees 2 theta, ±0.2°; (2) an X-ray powder diffraction (XRPD) pattern having one or more (e.g., 2, 4, 6, 8, 10, or all) of the following peaks: 9.7, 13.0, 18.2, 20.0, 21.4, 22.4, 24.1, 24.8, 26.0, 26.3, 27.5, and 28.4, degrees 2 theta, ±0.2°; (3) an XRPD pattern substantially the same as shown in FIG. 5A or Table 5; (4) a Differential Scanning calorimetry (DSC) pattern substantially the same as shown in FIG. 5B; or any combination thereof (e.g., (1) and (4), (2) and (4), (1), (2) and (4), or (3) and (4)). In some embodiments, the crystalline Form 2 can be characterized by an XRPD pattern having the major peaks (e.g., peaks with relative intensity of 20% or above, 30% or above, 40% or above, 50% or above, 60% or above, 70% or above, 80% or above, or 90% or above) of FIG. 5A or as shown in Table 5, degrees 2 theta, ±0.2°. In some embodiments, the crystalline Form 2 can be characterized by an XRPD pattern having all of the following peaks: 9.7, 13.0, 24.1, 26.0, and 26.3, degrees 2 theta, ±0.2°. In some embodiments, the crystalline Form 2 can also be characterized by a DSC pattern having an endothermic peak with an onset temperature of about 309.0° C. and/or a peak temperature of about 312.0° C. In some embodiments, the crystalline Form 2 can be further characterized by a DSC pattern having a broad endothermic peak from about 43° C. to about 122° C. As shown in the Examples section, Form 2 was determined to be a channel hydrate/solvate. In some embodiments, the crystalline Form 2 is substantially the same as the crystalline Form 2 obtained in Example 6 of this application.

The potassium salt of Compound 1 in crystalline Form 2 can be prepared by methods described herein. For example, in some embodiments, the potassium salt of Compound 1 in crystalline Form 2 can be prepared by a method comprising 1) mixing Compound 1 with a potassium base, e.g., aqueous potassium hydroxide, in a solvent (e.g., methanol) to form a suspension or solution, typically under heat, such as about 50° C.; and 2) cooling the suspension or solution to provide crystalline Form 2. As discussed herein, the potassium salt prepared in solvent containing minimal or no water typically results in crystalline Form 1. Thus, the method of preparation of Form 2 typically controls the reaction system to have some amount of water, for example, the solvent system typically should have a water content of more than 0.5% volume/volume, such as more than 1% v/v. The potassium base is typically used in slightly excess, such as at about 1.1 to about 1.5 molar equivalent of Compound 1. The suspension or solution is typically stirred for a period of time under heat, such as about 50° C. before the cooling step. In some embodiments, an antisolvent such as ethyl acetate can also be added. In some embodiments, the potassium salt of Compound 1 in crystalline Form 2 can also be prepared from Form 1, for example, by stirring Form 1 in a solvent system that has a water content of more than 0.5% volume/volume, such as more than 1% v/v.

Exemplified representative procedures for preparing potassium salt of Compound 1 in crystalline Form 2 are shown in Examples 6, 7 and 10 of this application.

In some embodiments, the potassium salt of Compound 1 can be in an amorphous form.

In some embodiments, the present disclosure also provides a solid form of the potassium salt of Compound 1 that can be produced by any of the applicable methods described in the Examples section. For example, in some embodiments, the potassium salt of Compound 1 can also exist in a crystalline form of Form 3, 4, 5, or 6. As discussed in the Examples section, each of Forms 3, 4, 5, or 6 was determined to be a solvate/hydrate. Characteristics of Forms 3, 4, 5, and 6 are described herein.

The potassium salt of Compound 1 herein is typically in a substantially pure form. For example, in some embodiments, the potassium salt of Compound 1 can have a purity of greater than 70%, preferably greater than 90% (e.g., greater than 95%, greater than 97%, greater than 98%, greater than 99%), by weight, by HPLC area, or both. In some embodiments, the potassium salt of Compound 1 can be characterized by a purity by weight and/or by HPLC area of about 70%, about 75%, about 80%, about 85%, about 90%, about 95%, about 97%, about 99%, about 99.5%, about 99.8%, or any ranges between the specified values. For example, in some embodiments, the potassium salt of Compound 1 can be characterized by a purity by HPLC area of about 70%, about 75%, about 80%, about 85%, about 90%, about 95%, about 97%, about 99%, about 99.5%, about 99.8%, or any ranges between the specified values. The substantially pure potassium salt of Compound 1 can be in a solid form (e.g., a crystalline form described herein, amorphous form, or a combination thereof) or in a solution, suspension, or another form. In some embodiments, the substantially pure potassium salt of Compound 1 can be in crystalline Form 1. For example, in some embodiments, the substantially pure potassium salt of Compound 1 can be in Form 1 substantially free of solid forms other than Form 1, for example, with less than 20% by weight, less than 10% by weight, or less than 5% by weight of solid forms other than Form 1, or no other solid form can be identified, for example, by XRPD. In some embodiments, the substantially pure potassium salt of Compound 1 or a pharmaceutical composition comprising the potassium salt of Compound 1 can include the potassium salt of Compound 1 solely in the form of Form 1, i.e., with no other solid form of the potassium salt of Compound 1 identifiable by XRPD. In some embodiments, the substantially pure potassium salt of Compound 1 can be in crystalline Form 2. For example, in some embodiments, the substantially pure potassium salt of Compound 1 can be in Form 2 substantially free of solid forms other than Form 2, for example, with less than 20% by weight, less than 10% by weight, or less than 5% by weight of solid forms other than Form 2, or no other solid form can be identified, for example, by XRPD. In some embodiments, the substantially pure potassium salt of Compound 1 or a pharmaceutical composition comprising the potassium salt of Compound 1 can include the potassium salt of Compound 1 solely in the form of Form 2, i.e., with no other solid form of the potassium salt of Compound 1 identifiable by XRPD. However, in some embodiments, the substantially pure potassium salt of Compound 1 can be in crystalline Form 1, an amorphous form, or a combination thereof. In some embodiments, the substantially pure potassium salt of Compound 1 can be in crystalline Form 2, an amorphous form, or a combination thereof. In some embodiments, the substantially pure potassium salt of Compound 1 can be in crystalline Form 1, crystalline Form 2, or a combination thereof. In some embodiments, the substantially pure potassium salt of Compound 1 can be in crystalline Form 1, crystalline Form 2, an amorphous form, or a combination thereof.

The substantially pure potassium salt of Compound 1 herein typically has a potassium content close to the theoretical potassium content calculated based on a molar ratio of potassium to Compound 1 of 1:1. In some embodiments, the substantially pure potassium salt of Compound 1 is characterized by a molar ratio of potassium to Compound 1 of about 1:1. In some embodiments, the substantially pure potassium salt of Compound 1 has a potassium content of about 80% to about 125% of the theoretical potassium content. Potassium content can be determined by known methods, such as by ion chromatography.

The substantially pure potassium salt of Compound 1 herein can be free or substantially free of Compound 1 (free acid), and/or can be free or substantially free of other salts of Compound 1. In some embodiments, the substantially pure potassium salt of Compound 1 is substantially free of Compound 1, for example, with an amount of less than 5% by weight (e.g., less than 3%, less than 1%, less than 0.2%, less than 0.1% or less than 0.05%). In some embodiments, the substantially pure potassium salt of Compound 1 is free of Compound 1, other than an amount that may exist through equilibrium. In some embodiments, the substantially pure potassium salt of Compound 1 has no detectable amount of Compound 1. In some embodiments, the substantially pure potassium salt of Compound 1 is substantially free of other salts of Compound 1, for example, with an amount less than 5% by weight (e.g., less than 3%, less than 1%, less than 0.2%, less than 0.1% or less than 0.05%). In some embodiments, the substantially pure potassium salt of Compound 1 includes no detectable amount of other salts of Compound 1.

As described in details herein, it was unexpectedly discovered that converting Compound 1 into its potassium salt can improve the initial purity of the "starting material" Compound 1. Converting Compound 1 into its sodium salt also improved the purity, however, to a lesser extent. As shown in Example 9, the potassium salt Form 1 can have a purity of about 99.5%, which is not achieved by either the free acid or the sodium salt. In some embodiments, the present disclosure also provides a method of purifying Compound 1, the method comprising converting Compound 1 into its sodium or potassium salt.

Also detailed in the Examples section, the potassium salt Form 1 or 2, sodium salt Form A and Compound 1 are all chemically and physically stable at 40° C./75% RH and 60° C. for 7 days. However, the potassium or sodium salt have much improved solubility in bio-relevant media compared to that of Compound 1 (free acid).

Other Salts of Compound 1

In some embodiments, the present disclosure is directed to an alkaline earth metal salt of Compound 1, such as a calcium salt or a magnesium salt. For example, in some embodiments, the alkaline earth salt can be a calcium salt of Compound 1, with the molar ratio of calcium to compound 1 of about 1:2. In some embodiments, the alkaline earth salt can be a magnesium salt of Compound 1, with the molar ratio of magnesium to compound 1 of about 1:2. The alkaline earth salts can be readily obtained, for example, by salt exchange from sodium or potassium salt of Compound 1 with $CaCl_2$ or $MgCl_2$.

The alkaline earth salt of Compound 1 can also be in a solid form, such as an amorphous form, a crystalline form, or a combination thereof. For example, in some embodiments, the alkaline earth salt of Compound 1 can be an amorphous form. In some embodiments, the alkaline earth salt of Compound 1 can be in a crystalline form, e.g., any of those described herein in the Examples section, such as Patten 1 or 2 of the calcium salt of Example 11, or Pattern 1 or 2 of the magnesium salt of Example 12. Characteristics of the calcium salt and magnesium salt are described herein. See e.g., FIGS. 6A-6D and 7A-7B.

In some embodiments, the present disclosure is directed to an alkali metal salt of Compound 1, which is other than the sodium or potassium salt described herein.

In some embodiments, the present disclosure is directed to an amine salt of Compound 1, such as ammonium salt, diethyl amine salt, etc.

Method of Synthesis

Certain embodiments are directed to a method of preparing Compound 1 or a pharmaceutically acceptable salt thereof.

In some embodiments, the method comprises:

a) coupling compound 1-5 with compound 1-6 to form a compound 1-7, 1-5

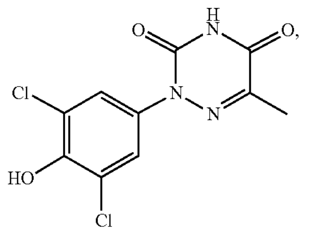

1-6

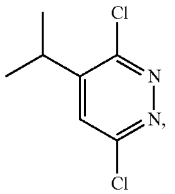

1-7

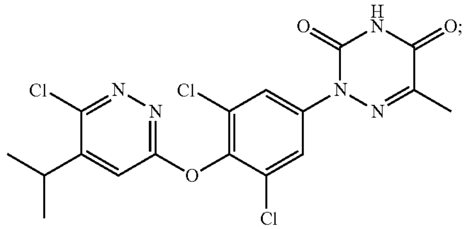

b) converting compound 1-7 into Compound 1; and c) optionally forming a pharmaceutically acceptable salt of Compound 1.

In some embodiments, the coupling of compound 1-5 with compound 1-6 can be carried out in the presence of a base (such as an inorganic carbonate base, e.g., $K_2CO_3$) and a copper catalyst. Typically, this coupling is carried out under heat. In some embodiments, converting compound 1-7 can be carried out in a hydrolysis condition, such as with water in acetic acid under heat. Exemplary conditions for the coupling of Compound 1-5 and 1-6 and the hydrolysis condition for converting compound 1-7 into Compound 1 are described herein. It should be noted that compounds 1-5, 1-6, and 1-7 are also novel and useful synthetic intermediates of the present disclosure.

In some embodiments, the method comprises reacting Compound 1 with a base (such as a sodium or potassium base) to form a salt of Compound 1.

Pharmaceutical Compositions

Certain embodiments are directed to a pharmaceutical composition comprising one or more of the compounds of the present disclosure.

The pharmaceutical composition can optionally contain a pharmaceutically acceptable excipient. In some embodiments, the pharmaceutical composition comprises one or more compounds of the present disclosure (e.g., Compound 1 in Form I or II, the sodium salt of Compound 1 in Form A, the potassium salt of Compound 1 in Form 1 or 2, an amorphous form of Compound 1, its sodium salt or potassium salt, or any combinations thereof) and a pharmaceutically acceptable excipient. In some embodiments, the pharmaceutical composition can be prepared by a method comprising mixing the one or more compounds of the present disclosure (e.g., Compound 1 in Form I or II, the sodium salt of Compound 1 in Form A, the potassium salt of Compound 1 in Form 1 or 2, an amorphous form of Compound 1, its sodium salt or potassium salt, or any combinations thereof) with the pharmaceutically acceptable excipient. Pharmaceutically acceptable excipients are known in the art. Non-limiting suitable excipients include, for example, encapsulating materials or additives such as absorption accelerators, antioxidants, binders, buffers, carriers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof. See also Remington's The Science and Practice of Pharmacy, 21st Edition, A. R. Gennaro (Lippincott, Williams & Wilkins, Baltimore, Md., 2005; incorporated herein by reference), which discloses various excipients used in formulating pharmaceutical compositions and known techniques for the preparation thereof.

The pharmaceutical composition can include any one or more of the compounds of the present disclosure. For example, in some embodiments, the pharmaceutical composition comprises Compound 1 in Form I or II, the sodium salt of Compound 1 in Form A, the potassium salt of Compound 1 in Form 1 or 2, an amorphous form of Compound 1, its sodium salt or potassium salt, or any combinations thereof, e.g., in a therapeutically effective amount. In some embodiments, the pharmaceutical composition can be prepared by a method comprising mixing the sodium salt of Compound 1 in Form A and/or an amorphous form of the sodium salt of Compound 1 with a pharmaceutically acceptable excipient. In some embodiments, the pharmaceutical composition can be prepared by a method comprising mixing the potassium salt of Compound 1 in Form 1 and/or an amorphous form of the potassium salt of Compound 1 with a pharmaceutically acceptable excipient. In some embodiments, the pharmaceutical composition can be prepared by a method comprising mixing the potassium salt of Compound 1 in Form 2 and/or an amorphous form of the potassium salt of Compound 1 with a pharmaceutically acceptable excipient.

In some specific embodiments, the pharmaceutical composition comprises the potassium salt of Compound 1. In some specific embodiments, the active ingredient in the pharmaceutical composition can comprise, consist essentially of, or consist of the potassium salt of Compound 1. In some embodiments, the pharmaceutical composition is substantially free of Compound 1 (as a free acid) and/or substantially free of another salt of Compound 1 other than potassium salt, for example, with Compound 1 and/or non-potassium salt of Compound 1 in an amount of less than 5% by weight (e.g., less than 3%, less than 1%, less than 0.2%, less than 0.1% or less than 0.05%).

In some specific embodiments, the pharmaceutical composition comprises Form 1 of the potassium salt of Compound 1. In some specific embodiments, the active ingredient in the pharmaceutical composition can comprise, consist essentially of, or consist of Form 1 of the potassium salt of Compound 1. In some embodiments, the potassium salt of Compound 1 exists in the pharmaceutical composition essentially in Form 1, for example, at least 80% (e.g., at least 85%, at least 90%, at least 95%) by weight of the total potassium salt of Compound 1 can exist in the pharmaceutical composition in Form 1. In some embodiments, the pharmaceutical composition is substantially free of Compound 1 (as a free acid) and/or substantially free of another salt of Compound 1 other than potassium salt, for example, with Compound 1 and/or non-potassium salt of Compound 1 in an amount of less than 5% by weight (e.g., less than 3%, less than 1%, less than 0.2%, less than 0.1% or less than 0.05%). In some embodiments, the pharmaceutical composition is substantially free of the potassium salt of Compound 1 in any other solid form, such as other crystalline forms including hydrates and solvates. In some embodiments, the pharmaceutical composition is free or substantially free of the potassium salt of Compound 1 in a crystalline form other than Form 1, for example, the pharmaceutical composition can in some embodiments include less than 10%, less than 5%, less than 2%, less than 1%, by weight of total the potassium salt of Compound 1, or non-detectable amount of the potassium salt of Compound 1 in a crystalline form other than Form 1.

In some specific embodiments, the active ingredient in the pharmaceutical composition can comprise, consist essentially of, or consist of the potassium salt of Compound 1 in Form 1, amorphous form, or a mixture thereof. In some embodiments, the potassium salt of Compound 1 can exist in the pharmaceutical composition as a mixture of Form 1 and an amorphous form, for example, at least 80% (e.g., at least 85%, at least 90%, at least 95%) by weight of the total potassium salt of Compound 1 can exist in the pharmaceutical composition in Form 1 or an amorphous form.

In some specific embodiments, the pharmaceutical composition comprises Form 2 of the potassium salt of Compound 1. In some specific embodiments, the active ingredient in the pharmaceutical composition can comprise, consist essentially of, or consist of Form 2 of the potassium salt of Compound 1. In some embodiments, the potassium salt of Compound 1 exists in the pharmaceutical composition essentially in Form 2, for example, at least 80% (e.g., at least 85%, at least 90%, at least 95%) by weight of the total potassium salt of Compound 1 can exist in the pharmaceutical composition in Form 2. In some embodiments, the pharmaceutical composition is substantially free of Compound 1 (as a free acid) and/or substantially free of another salt of Compound 1 other than potassium salt, for example, with Compound 1 and/or non-potassium salt of Compound 1 in an amount of less than 5% by weight (e.g., less than 3%, less than 1%, less than 0.2%, less than 0.1% or less than 0.05%). In some embodiments, the pharmaceutical composition is substantially free of the potassium salt of Compound 1 in any other solid form, such as other crystalline forms including hydrates and solvates. In some embodiments, the pharmaceutical composition is free or substantially free of the potassium salt of Compound 1 in a crystalline form other than Form 2, for example, the pharmaceutical composition can in some embodiments include less than 10%, less than 5%, less than 2%, less than 1%, by weight of the total potassium salt of Compound 1, or non-detectable amount of the potassium salt of Compound 1 in a crystalline form other than Form 2.

In some specific embodiments, the active ingredient in the pharmaceutical composition can comprise, consist essentially of, or consist of the potassium salt of Compound 1 in Form 2, amorphous form, or a mixture thereof. In some embodiments, the potassium salt of Compound 1 can exist in the pharmaceutical composition as a mixture of Form 2 and an amorphous form, for example, at least 80% (e.g., at least 85%, at least 90%, at least 95%) by weight of the total potassium salt of Compound 1 can exist in the pharmaceutical composition in Form 2 or an amorphous form.

In some specific embodiments, the pharmaceutical composition comprises the sodium salt of Compound 1. In some specific embodiments, the active ingredient in the pharmaceutical composition can comprise, consist essentially of, or consist of the sodium salt of Compound 1. In some embodiments, the pharmaceutical composition is substantially free of Compound 1 (as a free acid) and/or substantially free of another salt of Compound 1 other than sodium salt, for example, with Compound 1 and/or non-sodium salt of Compound 1 in an amount of less than 5% by weight (e.g., less than 3%, less than 1%, less than 0.2%, less than 0.1% or less than 0.05%).

In some specific embodiments, the pharmaceutical composition comprises Form A of the sodium salt of Compound 1. In some specific embodiments, the active ingredient in the pharmaceutical composition can comprise, consist essentially of, or consist of Form A of the sodium salt of Compound 1. In some embodiments, the sodium salt of Compound 1 exists in the pharmaceutical composition essentially in Form A, for example, at least 80% (e.g., at least 85%, at least 90%, at least 95%) by weight of the total sodium salt of Compound 1 can exist in the pharmaceutical composition in Form A. In some embodiments, the pharmaceutical composition is substantially free of Compound 1 (as a free acid) and/or substantially free of another salt of Compound 1 other than sodium salt, for example, with Compound 1 and/or non-sodium salt of Compound 1 in an amount of less than 5% by weight (e.g., less than 3%, less than 1%, less than 0.2%, less than 0.1% or less than 0.05%). In some embodiments, the pharmaceutical composition is substantially free of the sodium salt of Compound 1 in any other solid form, such as other crystalline forms. In some embodiments, the pharmaceutical composition is free or substantially free of the sodium salt of Compound 1 in a crystalline form other than Form A, for example, the pharmaceutical composition can in some embodiments include less than 10%, less than 5%, less than 2%, less than 1%, by weight of the total sodium salt of Compound 1, or non-detectable amount of the sodium salt of Compound 1 in a crystalline form other than Form A.

In some specific embodiments, the active ingredient in the pharmaceutical composition can comprise, consist essentially of, or consist of the sodium salt of Compound 1 in Form A, amorphous form, or a mixture thereof. In some embodiments, the sodium salt of Compound 1 can exist in the pharmaceutical composition as a mixture of Form A and an amorphous form, for example, at least 80% (e.g., at least 85%, at least 90%, at least 95%) by weight of the total sodium salt of Compound 1 can exist in the pharmaceutical composition in Form A or an amorphous form.

Pharmaceutical compositions described herein can be prepared by any method known in the art of pharmacology. In general, such preparatory methods include bringing the active ingredient, such as the salt of the present disclosure, into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients useful for the manufacture of the pharmaceutical compositions herein include, for example, inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

The pharmaceutical composition can also be formulated for delivery via any of the known routes of delivery, which include but are not limited to oral, parenteral, inhalation, etc.

In some embodiments, the pharmaceutical composition can be formulated for oral administration. The oral formulations can be presented in discrete units, such as capsules, pills, cachets, lozenges, or tablets, each containing a predetermined amount of the active compound; as a powder or granules; as a solution or a suspension in an aqueous or non-aqueous liquid; or as an oil-in-water or water-in-oil emulsion. Excipients for the preparation of compositions for oral administration are known in the art. Non-limiting suitable excipients include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient (e.g., the compounds of the present disclosure) can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Although the descriptions of pharmaceutical compositions provided herein are mainly directed to pharmaceutical compositions which are suitable for administration to humans, such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. For veterinary use, a compound of the present disclosure can be administered as a suitably acceptable formulation in accordance with normal veterinary practice. The veterinarian can readily determine the dosing regimen and route of administration that is most appropriate for a particular animal.

The compounds of the present disclosure are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

In some embodiments, all the necessary components for the treatment of a disease or disorder herein using a compound of the present disclosure either alone or in combination with another agent or intervention traditionally used for the treatment of such disease can be packaged into a kit. Specifically, in some embodiments, the present disclosure provides a kit for use in the therapeutic intervention of the disease comprising a packaged set of medicaments that include the compound disclosed herein as well as buffers and other components for preparing deliverable forms of said medicaments, and/or devices for delivering such medicaments, and/or any agents that are used in combination therapy with the compound of the present disclosure, and/or instructions for the treatment of the disease packaged with the medicaments. The instructions may be fixed in any tangible medium, such as printed paper, or a computer readable magnetic or optical medium, or instructions to reference a remote computer data source such as a world wide web page accessible via the internet.

In some embodiments, the pharmaceutical composition is formulated for parenteral administration (such as intravenous injection or infusion, subcutaneous or intramuscular injection). The parenteral formulations can be, for example, an aqueous solution, a suspension, or an emulsion. Excipients for the preparation of parenteral formulations are known in the art. Non-limiting suitable excipients include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof.

In some embodiments, the pharmaceutical composition is formulated for inhalation. The inhalable formulations can be, for example, formulated as a nasal spray, dry powder, or an aerosol administrable through a metered-dose inhaler. Excipients for preparing formulations for inhalation are known in the art. Non-limiting suitable excipients include, for example, lactose, talc, silicic acid, aluminum hydroxide, calcium silicates and polyamide powder, and mixtures of these substances. Sprays can additionally contain propellants, such as chlorofluorohydrocarbons and volatile unsubstituted hydrocarbons, such as butane and propane.

The pharmaceutical composition can include various amounts of the compounds of the present disclosure, depending on various factors such as the intended use and potency and selectivity of the compounds. In some embodiments, the pharmaceutical composition comprises a therapeutically effective amount of a compound of the present disclosure. In some embodiments, the pharmaceutical composition comprises a therapeutically effective amount of the compound of the present disclosure and a pharmaceutically acceptable excipient. As used herein, a therapeutically effective amount of a compound of the present disclosure is an amount effective to treat a disease or disorder as described herein, which can depend on the recipient of the treatment, the disease or disorder being treated and the severity thereof, the composition containing the compound, the time of administration, the route of administration, the duration of treatment, its rate of clearance and whether or not another drug is co-administered.

Method of Treatment

Compounds of the present disclosure are useful as therapeutic active substances for the treatment and/or prophylaxis of diseases or disorders that are modulated by thyroid hormone receptor agonists.

In some embodiments, the present disclosure provides a method of treating a disease or disorder in a subject in need thereof. In some embodiments, the method comprises administering a therapeutically effective amount of one or more compounds of the present disclosure (e.g., Compound 1 in Form I or II, the sodium salt of Compound 1 in Form A, the potassium salt of Compound 1 in Form 1 or 2, an amorphous form of Compound 1, its sodium salt or potassium salt, or any combinations thereof) or a therapeutically effective amount of a pharmaceutical composition described herein.

The administering herein is not limited to any particular route of administration. For example, in some embodiments, the administering can be orally, nasally, transdermally, pulmonary, inhalationally, buccally, sublingually, intraperintoneally, subcutaneously, intramuscularly, intravenously, rectally, intrapleurally, intrathecally and parenterally. In some embodiments, the administering is orally.

Various diseases or disorders can be treated by the methods herein. Non-limiting examples include obesity, hyperlipidemia, hypercholesterolemia, diabetes (e.g., type 2 diabetes), non-alcoholic steatohepatitis (NASH), fatty liver, non-alcoholic fatty liver disease (NAFLD), bone disease, thyroid axis alteration, atherosclerosis, a cardiovascular disorder, tachycardia, hyperkinetic behavior, hypothyroidism, goiter, attention deficit hyperactivity disorder, learning disabilities, mental retardation, hearing loss, delayed bone age, neurologic or psychiatric disease, thyroid cancer, and combinations thereof. In some embodiments, the disease or disorder can be a metabolic disease such as type 2 diabetes or hyperlipidemia. In some embodiments, the cardiovascular disease is a coronary artery disease.

In some embodiments, the method is for treating obesity, hyperlipidemia, hypercholesterolemia, diabetes (e.g., type 2 diabetes), non-alcoholic fatty liver disease (NAFLD), non-alcoholic steatohepatitis (NASH), liver steatosis, atherosclerosis, cardiovascular diseases, hypothyroidism and/or thyroid cancer, which method comprises administering to a subject in need thereof a therapeutically effective amount of one or more compounds of the present disclosure (e.g., Compound 1 in Form I or II, the sodium salt of Compound 1 in Form A, the potassium salt of Compound 1 in Form 1 or 2, an amorphous form of Compound 1, its sodium salt or potassium salt, or any combinations thereof) or a pharmaceutical composition described herein.

In some embodiments, the present disclosure provides a method of treating a liver disease or disorder such as a non-alcoholic fatty liver disease (NAFLD) and/or non-alcoholic steatohepatitis (NASH) in a subject in need thereof. In some embodiments, the method comprises administering to the subject a therapeutically effective amount of one or more compounds of the present disclosure (e.g., Compound 1 in Form I or II, the sodium salt of Compound 1 in Form A, the potassium salt of Compound 1 in Form 1 or 2, an amorphous form of Compound 1, its sodium salt or potassium salt, or any combinations thereof) or a pharmaceutical composition described herein. In some preferred embodiments, the liver disease or disorder is liver fibrosis, hepatocellular carcinoma, and/or liver steatosis. In some preferred embodiments, the liver disease or disorder is non-alcoholic fatty liver disease (NAFLD). In some preferred embodiments, the liver disease or disorder is non-alcoholic steatohepatitis (NASH).

In some embodiments, the present disclosure provides a method of treating a lipid disease or disorder in a subject in need thereof. In some embodiments, the method comprises administering to the subject a therapeutically effective amount of one or more compounds of the present disclosure (e.g., Compound 1 in Form I or II, the sodium salt of Compound 1 in Form A, the potassium salt of Compound 1 in Form 1 or 2, an amorphous form of Compound 1, its sodium salt or potassium salt, or any combinations thereof) or a pharmaceutical composition described herein. In some preferred embodiments, the lipid disease or disorder is hyperlipidemia and/or hypercholesterolemia.

Dosing regimen including doses can vary and be adjusted, which can depend on the recipient of the treatment, the disease or disorder being treated and the severity thereof, the composition containing the compound, the time of administration, the route of administration, the duration of treatment, the compound potency, its rate of clearance and whether or not another drug is co-administered.

Definitions

"Compound(s) of the present disclosure" as used herein refers to Compound 1, or a pharmaceutically acceptable salt thereof (including the sodium, potassium, calcium, magnesium salt described herein), including but not limited to an isolated form, a substantially pure form, and/or a solid form thereof, which include crystalline forms, amorphous forms, hydrates and/or solvates. In any of the embodiments described herein, unless specified or otherwise contrary from context, Compound(s) of the present disclosure can be Compound 1 in Form I or II, the sodium salt of Compound 1 in Form A, the potassium salt of Compound 1 in Form 1 or 2, an amorphous form of Compound 1, its sodium salt or potassium salt, or any combinations thereof. In any of the embodiments described herein, unless specified or otherwise contrary from context, Compound(s) of the present disclosure can be in a substantially pure form, e.g., as described herein.

As used herein, the singular form "a", "an", and "the", includes plural references unless it is expressly stated or is unambiguously clear from the context that such is not intended.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Headings and subheadings are used for convenience and/or formal compliance only, do not limit the subject technology, and are not referred to in connection with the interpretation of the description of the subject technology. Features described under one heading or one subheading of the subject disclosure may be combined, in various embodiments, with features described under other headings or subheadings. Further it is not necessarily the case that all features under a single heading or a single subheading are used together in embodiments.

As used herein, the term "about" modifying an amount related to the invention refers to variation in the numerical quantity that can occur, for example, through routine testing and handling; through inadvertent error in such testing and handling; through differences in the manufacture, source, or purity of ingredients employed in the invention; and the like. As used herein, "about" a specific value also includes the specific value, for example, about 10% includes 10%. Whether or not modified by the term "about", the claims include equivalents of the recited quantities. In one embodiment, the term "about" means within 20% of the reported numerical value.

The terms "purity" and "impurities" are used according to their respective art accepted meaning. The terms "purity by HPLC", "HPLC purity," and iterations thereof are used to refer to the purity of the respective compound as measured using an HPLC method, e.g., the HPLC method described in the Examples section, expressed as HPLC area percentage. In any of the embodiments described herein, unless otherwise specified or contrary from context, the HPLC purity of a compound of the present disclosure can be measured in accordance with the HPLC Method described in Table B of Example 1 in the Examples section, and expressed as the area percentage of the peak representing the compound in an HPLC trace using 281 nm as the detection wavelength.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art.

The term "subject" (alternatively referred to herein as "patient") as used herein, refers to an animal, preferably a mammal, most preferably a human, who has been the object of treatment, observation or experiment.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound described herein to a subject in need of such treatment.

EXAMPLES

The various starting materials, intermediates, and compounds of the preferred embodiments can be isolated and purified where appropriate using conventional techniques such as precipitation, filtration, crystallization, evaporation, distillation, and chromatography. Characterization of these compounds can be performed using conventional methods such as by melting point, mass spectrum, nuclear magnetic resonance, and various other spectroscopic analyses. Exemplary embodiments of steps for performing the synthesis of products described herein are described in greater detail infra.

Example 1. General Methods

Materials: the starting materials, reagents, solvents, etc. are generally available through commercial sources.

$^{1}$H NMR was performed using Bruker Advance 300 equipped with automated sampler (B-ACS 120).

Powder X-Ray Diffraction (XRPD): XRPD patterns were identified with an X-ray diffractometer (Bruker D8 advance or PANalytical Aeris). The system was equipped with LynxEye detector, with wavelength 1.5418 Å. Samples were scanned from 3 to 40° 2θ, at a step size 0.02° 2θ. The tube voltage and current were 40 KV and 40 mA, or 7.5 mA (PANalytical Aeris), respectively.

DSC Analysis: DSC was performed using a DSC Q200 or Discovery DSC 250 (TA Instruments, US). The sample was placed into an aluminum pin-hole hermetic pan and the weight was accurately recorded. The sample was heated at a rate of 10° C./min from 25° C. to the final temperature.

TGA Analysis: TGA was carried out on a TGA Q500 or Discovery TGA 55 (TA Instruments, US). The sample was placed into an open tared aluminum pan, automatically weighed, and inserted into the TGA furnace. The sample was heated at a rate of 10° C./min from ambient temperature to the final temperature.

Polarizing Microscope Analysis (PLM): Light microscopy was performed using a Polarizing Microscope ECLIPSE LV100POL (Nikon, JPN).

Dynamic Vapor Sorption (DVS): Moisture sorption/desorption data was collected on a IGASorp DVS. The sample was placed into a tarred sample chamber and weighed automatically. The sample was dried at 50° C. until the % RH was less than 0.3% and cooled to 25° C. Set the instrument parameters as below.

| | |
|---|---|
| Mode: | F1 |
| Min time (min): | 30 min |
| Timeout (min): | 120 min |
| Sample temperature: | 25° C. |
| Temperature stability: | 0.1° C./min |
| Cycle: | Full cycle |
| Adsorption: | 0, 10, 20, 30, 40, 50, 60, 70, 80, 90 |
| Desorption: | 80, 70, 60, 50, 40, 30, 20, 10, 0 |
| Flow rate: | 250 mL/min |
| Scans: | 2 |
| Wait until: | 98% |

High Performance Liquid Chromatography (HPLC)

HPLC analysis was performed with an Agilent HPLC 1260 series instrument. HPLC method for solubility and stability/purity testing was listed in Tables A and B.

TABLE A

| HPLC Method for Solubility Test | |
|---|---|
| Column | Agilent XDB-C18, 4.6*50 mm, 1.8 μm |
| Mobile Phase | A: 0.01% TFA in water<br>B: ACN |
| Gradient (T/B %) | 0/45%, 7/50%, 8/100% |
| Column Temperature | 40° C. |
| Detector | DAD; 281 nm |
| Flow Rate | 1.2 mL/min |
| Injection Volume | 3 μL |
| Run Time | 8 min |
| Post Time | 2 min |
| Diluent | DMSO |

TABLE B

| HPLC Method for Stability/Purity Test | |
|---|---|
| Column | Agilent XDB-C18, 4.6*50 mm, 1.8 μm |
| Mobile Phase | A: 0.01% TFA in water<br>B: ACN |
| Gradient (T/B %) | 0/10%, 5/45%, 8/50%, 10/100%, 12/100% |
| Column Temperature | 40° C. |
| Detector | DAD; 281 nm |
| Flow Rate | 1.2 mL/min |
| Injection Volume | 5 μL |
| Run Time | 12 min |
| Post Time | 2 min |
| Diluent | DMSO |

Example 2. Synthesis of Compound 1

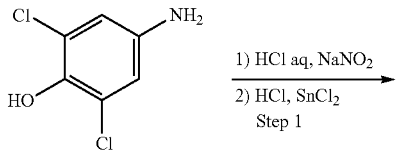

1-1

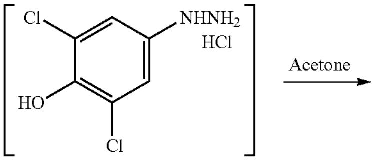

1-2

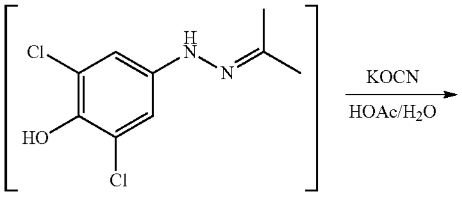

1-3

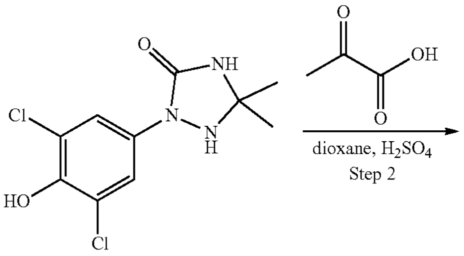

1-4

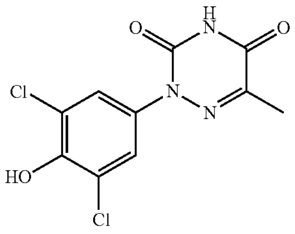

1-5

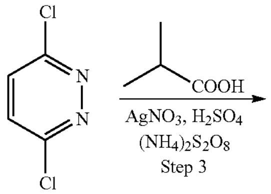

-continued

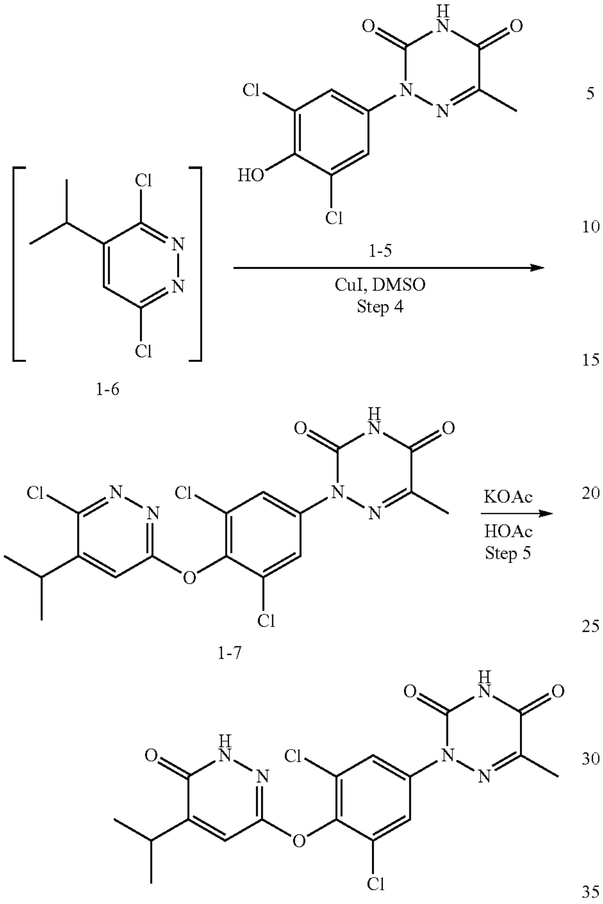

1

Step 1: To a solution of 1-1 (43 g, 0.242 mol) in HCl (84 mL) was added a solution of $NaNO_2$ (17.5 g, 0.254 mol) in water (86 mL) at −5° C. After stirring for 0.5-1 hour, a solution of $SnCl_2$ (68.8 g, 0.363 mol) in HCl (147 mL) was added at 0° C. After 0.5 h, acetone (70.3 g, 1.21 mol) was added, and the mixture was stirred for 1 hour. Filtered and the filter cake was washed with water. The wet solid was dissolved in HOAc (107.5 mL), and to the solution was added a solution of KOCN (20.6 g, 0.254 mol) in water (64.5 mL). The mixture was stirred for 1 hour and filtered. The filter cake was washed with water and dried to afford 1-4.

Step 2: To a solution of 1-4 (80 g, 0.290 mol) in 1,4-dioxane (800 mL) was added pyruvic acid (30.6 g, 0.347 mol) and $H_2SO_4$ (14.5 g, 0.145 mol). The mixture was heated at 55° C. for 12 hours and then filtered. To the filtrate was added water (1.6 L) to precipitate. Filtered, and the filter cake was slurried in isopropanol to afford 1-5.

Step 3: A mixture of 3,6-dichloropyridazine (40 g, 0.269 mol), $AgNO_3$ (9.2 g, 0.054 mol), isobutyric acid (26 g, 0.295 mol) and $H_2SO_4$ (13.2 g, 0.132 mol) in water was heated at 55° C. At the same temperature was added a solution of $(NH_4)_2S_2O_8$ (92 g, 0.403 mol) in water (200 mL). The mixture was heated to 55° C. for 1 hour and then cooled. To the mixture was added ammonium hydroxide and DCM, and then separated. The organic phase was dried with $Na_2SO_4$, filtered and concentrated to afford crude 1-6 which was used for next step without purification.

Step 4: A mixture of 1-5 (40 g, 0.139 mol), 1-6 (43.7 g, 0.229 mol), $K_2CO_3$ (38.4 g, 0.278 mol) and CuI (5.3 g, 0.028 mol) in DMSO (400 mL) was heated at 120° C. for 2 days, and then cooled. A solution of KOH (15.6 g) in MeOH (400 mL) was added and the mixture was filtered. The filtrate was added into HCl (400 mL) and the mixture was filtered. The filter cake was washed with water and slurried in MeCN/EtOH. The mixture was filtered and the filter cake was dried to afford 1-7.

Step 5: A mixture of 1-7 (25 g, 0.056 mol), KOAc (11.1 g, 0.113 mol) and water (1.5 g, 0.083 mol) in HOAc (250 mL) was heated at reflux for 30 hours, and then cooled. The mixture was filtered and the filter cake was slurried in DMSO/water, filtered and dried to give 1.

Figure 1C:
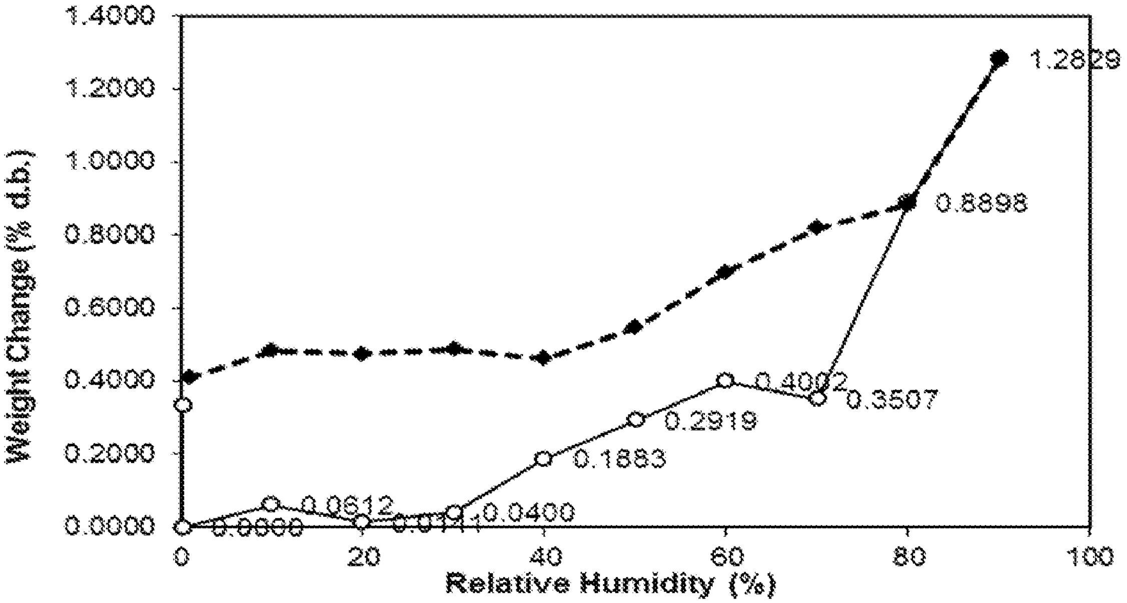
FIG. 1C shows a representative Dynamic Vapor Sorption (DVS) spectrum of crystalline Form I of Compound 1.

The solid state of Compound 1 was characterized and assigned as Form I of Compound 1. Representative spectra of XRPD, DSC, and DVS are shown in FIGS. 1A-1C. See also Table 1 for a listing of XRPD peaks. Form I was found to have high crystallinity. The melting temperature was observed at about 334 to 336° C. by DSC, and TGA showed no obvious weight loss from RT to 200° C. $^1$H NMR result suggested the sample had no residual solvent. Form I is an anhydrous form. Form I was found to be slightly hygroscopic with 0.9% water uptake at 0 to 80% RH, and crystal form of the solid remained unchanged, the XRPD pattern was not changed after the DVS study.

TABLE 1

Listing of XRPD peaks of Form I of Compound 1

| Angle 2-Theta ° | Intensity % % | Intensity Count | d value Angstrom |
|---|---|---|---|
| 8.096 | 13.2 | 153 | 10.91219 |
| 10.782 | 59.4 | 686 | 8.19919 |
| 12.166 | 55.8 | 644 | 7.26909 |
| 12.375 | 64.8 | 749 | 7.1468 |
| 12.926 | 11.6 | 134 | 6.84314 |
| 13.321 | 14.8 | 171 | 6.64136 |
| 13.581 | 15.3 | 177 | 6.51469 |
| 14.016 | 100 | 1155 | 6.31363 |
| 16.353 | 9.4 | 109 | 5.41599 |
| 16.543 | 11.8 | 136 | 5.35431 |
| 17.055 | 39.9 | 461 | 5.19486 |
| 17.376 | 18.2 | 210 | 5.0994 |
| 17.779 | 35 | 404 | 4.98469 |
| 19.524 | 8.4 | 97 | 4.54316 |
| 20.139 | 23.3 | 269 | 4.40576 |
| 20.396 | 24.8 | 287 | 4.35074 |
| 21.1 | 10.8 | 125 | 4.20712 |
| 21.343 | 9.1 | 105 | 4.15971 |
| 21.967 | 18.1 | 209 | 4.04305 |
| 22.619 | 37 | 427 | 3.92787 |
| 23.081 | 14.5 | 168 | 3.85029 |
| 23.586 | 37.1 | 429 | 3.76903 |
| 24.165 | 10 | 116 | 3.68005 |
| 24.622 | 35.2 | 406 | 3.61279 |
| 25.041 | 28.7 | 331 | 3.55329 |
| 25.448 | 51.8 | 598 | 3.49732 |
| 25.986 | 38.4 | 443 | 3.42613 |
| 26.92 | 10.2 | 118 | 3.30933 |
| 27.482 | 8.3 | 96 | 3.24293 |
| 28.072 | 14.5 | 168 | 3.17606 |
| 28.337 | 17.1 | 197 | 3.14695 |
| 28.75 | 43.7 | 505 | 3.10275 |
| 29.601 | 13.3 | 154 | 3.0154 |
| 30.022 | 16.2 | 187 | 2.97409 |
| 30.346 | 12.4 | 143 | 2.94304 |
| 30.94 | 17.3 | 200 | 2.88789 |
| 31.414 | 6.9 | 80 | 2.84541 |
| 32.433 | 7.1 | 82 | 2.75826 |
| 33.104 | 12.6 | 145 | 2.70386 |
| 34.192 | 13.9 | 160 | 2.62033 |
| 34.794 | 10.2 | 118 | 2.57631 |
| 36.113 | 7.7 | 89 | 2.48523 |
| 37.39 | 7.2 | 83 | 2.40318 |
| 38.127 | 9.2 | 106 | 2.35842 |

TABLE 1-continued

| Listing of XRPD peaks of Form I of Compound 1 | | | |
|---|---|---|---|
| Angle 2-Theta ° | Intensity % % | Intensity Count | d value Angstrom |
| 38.684 | 7.2 | 83 | 2.32574 |
| 39.432 | 7.8 | 90 | 2.28331 |

Physical stability of Form I was evaluated upon grinding and high humidity (RT/92.5% RH for 24 days). For mechanical treatment study, Form I (10 mg) was ground manually for 5 min, and the sample was analyzed by XRPD after grinding for 2 and 5 min, respectively. The crystal form remained unchanged after grinding, while the crystallinity was significantly decreased after grinding. For stability upon high humidity, no form change was observed, Form I was physically stable under high humidity condition for 24 days.

Example 3. Polymorph Screening of Compound 1

Compound 1 was screened for polymorphs using several technics: slurry, cooling crystallization, and anti-solvent precipitation, etc.

In the slurry study, appropriate amounts of Compound 1 (Form I) were weighed into sample vials and solvents were added to make suspensions at the concentration of 12.5 mg/mL. All suspensions were shaken or stirred at RT, 50° C. and 60° C. for 3 to 5 days. Then, each suspension was filtered and the filter cake was analyzed by XRPD. Solvents used for this study include: MeOH, EtOH, IPA (isopropyl alcohol), n-butanol, MEK (methyl ethyl ketone or 2-butanone), dichloromethane/MeOH (1:1), MeOH (10% water), ACN (10% water), THF (10% water), EtOH (10% water), Acetone (10% water), THF (tetrahydrofuran), n-Heptane, ACN (acetonitrile), MTBE (methyl tert-Butyl ether), Acetone, Water, Toluene, EA (ethyl acetate), and IPAC (isopropyl acetate). No new form was found.

For the cooling crystallization, about 15 mg of Compound 1 (Form I) was weighed into sample vials and 500 μL of different solvents were added to obtained suspensions at 50° C., respectively. Then, DMSO was added, 50 to 100 μL per time, until the mixture was nearly clear. After stirring for about 30 min, the hot filtrates were used for slow and fast cooling crystallization. For slow cooling, the filtrates were placed in the Crystal 16 reactor to cool from 50° C./60° C. to −5° C. at a rate of 0.1° C./min and aged for 48 hours. Any obtained solids were characterized accordingly. For fast cooling, the filtrates were placed in the refrigerator and cooled to 5° C. immediately. If no solid appeared after 1 to 2 days, the filtrates would be cooled to −20° C. in refrigerator. Any obtained solids were characterized accordingly. Solvents used for this study (other than DMSO) include MeOH, EA, ACN, IPAC, EtOH, MEK, MTBE, Water, Acetone, IPA, THF, Toluene, and n-Butanol. Solids were obtained in IPAC/DMSO, water/DMSO, MTBE/DMSO and toluene/DMSO by slow cooling crystallization and in MTBE/DMSO, water/DMSO by fast cooling crystallization. All solids obtained were Form II. Therein, the XRPD pattern of the solid obtained in toluene/DMSO was similar to Form II with several few peaks, which might be due to the residual solvent.

Anti-solvent precipitations were carried out by normal and by reverse addition. For normal addition, about 15 mg of Compound 1 (Form I) was dissolved in DMSO at RT to make a clear solution. The drug solutions were filtered and the filtrates were distributed into sample vials. Then anti-solvent was added gradually to obtain the precipitation. If precipitation occurred, products were characterized accordingly. For reverse addition, Compound 1 (Form I) was weighed into 230 μL of DMSO to make a clear solution. After filtration, the filtrates were added into 2.3 mL of anti-solvents by dropwise respectively. If precipitation occurred, products were characterized accordingly. Antisolvents used are MeOH, EA, ACN, IPAC, EtOH, MEK, MTBE, Water, Acetone, IPA, THF, Toluene, or n-Butanol. In most experiments, Form I was obtained, while Form II was obtained from DMSO-MTBE by normal addition and MTBE-DMSO, IPAC-DMSO by reverse addition precipitation.

During screening, a new XRPD pattern was initially identified from anti-solvent precipitation in DMSO/MTBE, and assigned as Form II with representative XRPD spectrum and data in FIG. 2A and Table 2. Form II was also obtained from other crystallization experiments including reverse anti-solvent addition in MTBE/DMSO and IPAC/DMSO, slow cooling crystallization in IPAC/DMSO, MTBE/DMSO and toluene/DMSO, and fast cooling crystallization in MTBE/DMSO and water/DMSO.

TABLE 2

| Listing of XRPD Peaks of Form II of Compound 1 | | | |
|---|---|---|---|
| Angle 2-Theta ° | Intensity % % | Intensity Count | d value Angstrom |
| 5.152 | 38.1 | 321 | 17.1376 |
| 9.451 | 19.6 | 165 | 9.3505 |
| 9.909 | 42.6 | 359 | 8.91886 |
| 10.771 | 42.8 | 361 | 8.20724 |
| 12.055 | 25 | 211 | 7.33595 |
| 12.707 | 20.4 | 172 | 6.96057 |
| 13.164 | 17.1 | 144 | 6.72014 |
| 16.452 | 26.7 | 225 | 5.38379 |
| 16.678 | 46.4 | 391 | 5.31126 |
| 17.634 | 48.9 | 412 | 5.02537 |
| 18.441 | 25.1 | 212 | 4.80733 |
| 18.852 | 48.8 | 411 | 4.70355 |
| 19.771 | 100 | 843 | 4.48691 |
| 20.137 | 60.7 | 512 | 4.40604 |
| 20.739 | 92.4 | 779 | 4.27954 |
| 21.172 | 41 | 346 | 4.19304 |
| 21.591 | 35.2 | 297 | 4.11252 |
| 22.321 | 31 | 261 | 3.97965 |
| 22.498 | 49 | 413 | 3.9487 |
| 22.732 | 80 | 674 | 3.9087 |
| 23.428 | 28.5 | 240 | 3.79412 |
| 23.703 | 67.4 | 568 | 3.75066 |
| 24.048 | 54.1 | 456 | 3.69765 |
| 24.808 | 31.6 | 266 | 3.5861 |
| 25.124 | 21 | 177 | 3.54166 |
| 25.829 | 18.7 | 158 | 3.44654 |
| 26.221 | 22.4 | 189 | 3.39595 |
| 26.461 | 59.1 | 498 | 3.36563 |
| 26.731 | 45.6 | 384 | 3.33228 |
| 27.663 | 19.2 | 162 | 3.22215 |
| 28.146 | 36.4 | 307 | 3.16789 |
| 28.406 | 28.5 | 240 | 3.13945 |
| 28.654 | 25.9 | 218 | 3.11293 |
| 29.673 | 33.9 | 286 | 3.00829 |
| 30.307 | 23.8 | 201 | 2.94678 |
| 30.683 | 32 | 270 | 2.9115 |
| 31.14 | 18.5 | 156 | 2.86979 |
| 31.947 | 22.4 | 189 | 2.79914 |
| 32.886 | 22.5 | 190 | 2.72134 |
| 33.507 | 17.8 | 150 | 2.67232 |
| 34.501 | 19.2 | 162 | 2.59757 |
| 35.841 | 16.1 | 136 | 2.50343 |
| 37.821 | 15.1 | 127 | 2.37678 |
| 38.19 | 15.9 | 134 | 2.35469 |

TABLE 2-continued

Listing of XRPD Peaks of Form II of Compound 1

| Angle 2-Theta ° | Intensity % % | Intensity Count | d value Angstrom |
|---|---|---|---|
| 39.171 | 13.5 | 114 | 2.29792 |
| 39.534 | 13.3 | 112 | 2.27766 |

Form II was characterized after being dried under vacuum at 50° C. for 3 hours. The sample was irregular shaped crystal. About 23% of residual DMSO was detected by $^1$H-NMR, corresponding to the weight loss at 55 to 150° C. observed by TGA, see FIG. 2B. One sharp endothermic peak attributed to melting and two broad endothermic peaks were observed by DSC, see FIG. 2B. The theoretical DMSO content of 1 mol DMSO solvate, i.e., the solvate has a molar ratio of DMSO to Compound 1 of 1:1, is 15.6%. Hence, Form II was a solvate having a molar ratio of DMSO to Compound 1 of 1.5:1.

To investigate whether the second endothermic peak in DSC thermogram of Form II was due to desolvation or form transition, Form II sample was heated to 83° C. and 135° C. by DSC, respectively, and the sample was both converted to Form I by XRPD. Although the XRPD pattern of the sample after heated to 83° C. was consistent with that of Form I, it still had 10% weight loss by TGA and ~1 mol of DMSO by $^1$H-NMR. Hence, for Form II, DMSO should be lost in 2 steps, while the crystal form changed after losing ~0.5 mol of DMSO.

In addition, slurry study of Form II was performed in MeOH, ACN, acetone, EA and water at 50° C., respectively. It was found that Form II completely converted to Form I after 1 day in all experiments, suggesting that Form II can be easily converted to Form I.

Example 4. Preparation of Sodium Salt of Compound 1

Compound 1 (150.23 mg) was stirred in 2.25 mL of MeOH at 50° C. for 10 min, and then 1.2 eq of aqueous NaOH solution was added. The suspension was kept stirring at 50° C. for 3 hours, and then cooled to 25° C. and stirred for another 1 hour. Filtered and the filter cake was dried to afford sodium salt in Form A with a yield of 69%.

The sodium salt in Form A was characterized. Representative XRPD, DSC, and DVS spectra were shown in FIGS. 3A-3C. Table 3 below shows a listing of XRPD peaks of Form A of the sodium salt. Form A was determined to be an anhydrous form. It appeared that Form A typically contains certain residue solvent, such as methanol. As shown in the representative DSC spectrum, there was no endothermic peak before 380° C. The TGA spectrum shows that there was about 0.8% of weight loss from room temperature to about 250° C. The DVS study shows that Form A is slightly hygroscopic with about 1.6% of weight gain at 80% RH.

TABLE 3

Listing of XRPD Peaks of Form A of Sodium Salt of Compound 1

| Pos. [°2θ] | d-spacing [Å] | Height [cts] | Rel. Int. [%] |
|---|---|---|---|
| 7.2886 | 12.12884 | 673.47 | 48.51 |
| 9.0436 | 9.77865 | 78.44 | 5.65 |
| 10.6664 | 8.29429 | 1153.28 | 83.08 |
| 11.3091 | 7.82434 | 1388.21 | 100 |
| 12.1664 | 7.27486 | 109.07 | 7.86 |
| 14.4982 | 6.10964 | 916.65 | 66.03 |
| 15.0238 | 5.89708 | 290.39 | 20.92 |
| 15.711 | 5.64065 | 225.79 | 16.27 |
| 16.5972 | 5.3414 | 238.34 | 17.17 |
| 17.5483 | 5.054 | 523.19 | 37.69 |
| 18.0437 | 4.91635 | 75.14 | 5.41 |
| 18.5583 | 4.78117 | 117.59 | 8.47 |
| 19.2356 | 4.61431 | 1224.02 | 88.17 |
| 19.4706 | 4.55914 | 513.87 | 37.02 |
| 20.1131 | 4.41493 | 56.13 | 4.04 |
| 22.0152 | 4.03761 | 141.04 | 10.16 |
| 22.503 | 3.95118 | 1308.9 | 94.29 |
| 23.3341 | 3.81229 | 271.5 | 19.56 |
| 23.8376 | 3.7329 | 696.31 | 50.16 |
| 24.4485 | 3.64098 | 559.79 | 40.32 |
| 25.56 | 3.48513 | 631.69 | 45.5 |
| 25.9145 | 3.43824 | 202.99 | 14.62 |
| 26.7163 | 3.33685 | 157.53 | 11.35 |
| 27.1168 | 3.28847 | 1345.58 | 96.93 |
| 28.6117 | 3.11996 | 656.02 | 47.26 |
| 29.0031 | 3.07875 | 586.39 | 42.24 |
| 30.6531 | 2.91668 | 97.74 | 7.04 |
| 31.6648 | 2.82577 | 100.72 | 7.26 |
| 32.1345 | 2.78553 | 247.55 | 17.83 |
| 32.7837 | 2.73183 | 112.05 | 8.07 |
| 33.0797 | 2.70806 | 159.68 | 11.5 |
| 34.7041 | 2.58494 | 74.47 | 5.36 |
| 35.2397 | 2.54687 | 215.59 | 15.53 |
| 36.7945 | 2.44274 | 228.22 | 16.44 |
| 37.1697 | 2.41894 | 109.77 | 7.91 |
| 37.5173 | 2.39732 | 134.49 | 9.69 |
| 38.9918 | 2.30999 | 80 | 5.76 |
| 39.6921 | 2.27084 | 86.12 | 6.2 |

Example 5. Preparation of Form 1 of Potassium Salt of Compound 1

Compound 1 (111.7 mg) and KOH solid (17.73 mg) were added to 0.55 mL of MeOH at 50° C. The suspension was stirred for 3 hours and then cooled to 25° C. Ethyl acetate (1.1 mL) was added and stirred for another 2 hours. Solid was collected by filtration to afford potassium salt in Form 1 with a yield of 67%.

The potassium salt in Form 1 was characterized. Representative XRPD, DSC, and DVS spectra were shown in FIGS. 4A-4C. Table 4 below shows a listing of XRPD peaks of Form 1 of the potassium salt. Form 1 was determined to be an anhydrous form. As shown in the representative TGA spectrum, 0.36% of weight loss was observed from RT to 250° C. As shown in FIG. 4B, the DSC showed an endothermic peak with an onset of about 340° C., and a peak of about 343.6° C. Form 1 was slight hygroscopic with 1.8% of water uptake at 80% RH (see DVS spectrum of FIG. 4C) and the crystal form of solid remained unchanged after the DVS study. When Form 1 was grinded, although the XRPD pattern remained unchanged, crystallinity decreased after grinding for 5 min.

TABLE 4

Listing of XRPD peaks of Form 1 of Potassium Salt of Compound 1

| Pos. [°2θ] | d-spacing [Å] | Height [cts] | Rel. Int. [%] |
|---|---|---|---|
| 7.1676 | 12.33335 | 219.25 | 33.12 |
| 9.0348 | 9.78819 | 49.56 | 7.49 |
| 10.6173 | 8.33256 | 629.59 | 95.09 |
| 11.1425 | 7.94094 | 662.07 | 100 |
| 14.3382 | 6.17749 | 337.68 | 51 |
| 15.3748 | 5.76321 | 34.6 | 5.23 |
| 16.304 | 5.43682 | 44.87 | 6.78 |
| 17.2388 | 5.14403 | 137.61 | 20.78 |
| 18.0803 | 4.90648 | 145.49 | 21.97 |
| 18.9428 | 4.68498 | 502.14 | 75.84 |
| 21.5423 | 4.12515 | 85.27 | 12.88 |
| 22.2612 | 3.99354 | 386.84 | 58.43 |
| 22.7116 | 3.91535 | 66.29 | 10.01 |
| 23.2947 | 3.81865 | 342.41 | 51.72 |
| 24.045 | 3.70117 | 243.84 | 36.83 |
| 25.2395 | 3.52865 | 270.77 | 40.9 |
| 26.5606 | 3.35606 | 368.48 | 55.66 |
| 27.1555 | 3.28388 | 72.64 | 10.97 |
| 28.1755 | 3.16727 | 152.96 | 23.1 |
| 28.7107 | 3.10943 | 174.05 | 26.29 |
| 31.3661 | 2.85199 | 61.17 | 9.24 |
| 32.5266 | 2.75284 | 189.4 | 28.61 |
| 34.8173 | 2.57679 | 142.47 | 21.52 |
| 36.5226 | 2.4603 | 133.56 | 20.17 |
| 38.0471 | 2.36515 | 21.06 | 3.18 |

Example 6. Preparation of Form 2 of Potassium Salt of Compound 1

Compound 1 (149.59 mg) was suspended in 0.45 mL of MeOH at 50° C. and 1.2 eq of aqueous KOH solution was added. The suspension was kept stirring at 50° C. for 1 hour, and then cooled to 25° C. and stirred for another 1 hour. Ethyl acetate (1.35 mL) was added and the suspension was stirred for another 1 hour. Solid was collected by filtration to afford potassium salt in Form 2 with a yield of 55%.

The potassium salt in Form 2 was characterized. Representative XRPD, DSC, and DVS spectra were shown in FIGS. 5A-5C. Table 5 below shows a listing of XRPD peaks of Form 2 of the potassium salt. As shown in the representative TGA spectrum, 1.2% of weight loss was observed from RT to 250° C. 0.6% of MeOH was observed by NMR. The sample was heated to 225° C. by TGA for desolvation or dehydration. After desolvation or dehydration, the XRPD pattern of the sample was unchanged. However, when the "desolvated" or "dehydrated" sample was retested in TGA, we observed about 0.8% of weight loss from RT to about 200° C. As shown in FIG. 5B, there were two endothermic peaks in DSC with a broad first peak from about 43 to 122° C., which was believed to be due to desolvation or dehydration. The second peak at 312° C. might be due to melting. Form 2 may be a channel hydrate/solvate, and it was slight hygroscopic with 1.6% of water uptake at 80% RH (see DVS spectrum of FIG. 5C) and the crystal form of solid remained unchanged after the DVS study.

TABLE 5

Listing of XRPD Peaks of Form 2 of Potassium Salt of Compound 1

| Pos. [°2θ] | d-spacing [Å] | Height [cts] | Rel. Int. [%] |
|---|---|---|---|
| 6.4777 | 13.6453 | 56.13 | 17.46 |
| 9.6942 | 9.12382 | 166.19 | 51.68 |
| 13.0039 | 6.80819 | 129.85 | 40.38 |
| 17.0439 | 5.20241 | 54.2 | 16.86 |
| 18.1552 | 4.8864 | 111.11 | 34.55 |
| 20 | 4.43966 | 59.14 | 18.39 |
| 21.3718 | 4.15769 | 102.36 | 31.83 |
| 22.3873 | 3.97133 | 116.7 | 36.29 |
| 24.099 | 3.693 | 219.19 | 68.16 |
| 24.8496 | 3.58312 | 85.12 | 26.47 |
| 25.9729 | 3.43065 | 229.54 | 71.38 |
| 26.3462 | 3.38288 | 321.57 | 100 |
| 27.4763 | 3.24626 | 76.03 | 23.64 |
| 28.4353 | 3.13892 | 84.64 | 26.32 |
| 30.1178 | 2.96729 | 51.49 | 16.01 |
| 33.1105 | 2.70561 | 34.99 | 10.88 |
| 34.2791 | 2.61601 | 34.6 | 10.76 |
| 38.4116 | 2.34354 | 18.91 | 5.88 |

Example 7. Interconversion of Different Forms of Potassium Salt of Compound 1

Interconversion study were performed in MeOH/EA (1/9, RT or 50° C.) and acetone/water (20/1, RT or 50° C.). Equal amounts of Form 1 and Form 2 were slurried in specified solvents at different temperatures for certain time. The results showed that Form 1 was more stable in non-aqueous system and Form 2 was more stable in aqueous solution. The results were summarized in Table 6A.

TABLE 6A

Interconversion Study of Potassium Salts Form 1 and 2

| Temperature | Solvent | Condition | XRPD result |
|---|---|---|---|
| RT | MeOH/EtOAc (1/9), 20 V | Stirred overnight | Form 1 |
| | Acetone/Water (19/1), 20 V | Stirred overnight | Form 2 |
| 50° C. | MeOH/EtOAc (1/9), 20 V | Stirred overnight | Form 1 |
| | Acetone/Water (19/1), 20 V | Stirred overnight | Form 2 |

Form 1 was further tested to determine the influence of water on the crystalline form. Thus, 15 mg of potassium salt Form 1 was added into 0.3 mL of MeOH/water (with various amounts of water), and then the suspension was kept stirring at 25° C. for 24 h. The solid was collected by filtration and characterized by XRPD. As shown in Table 6B below, Form 1 (anhydrate) has the tendency to convert to Form 2 (hydrate) at >0.01 water activity (0.5% of water content) after 24 h. Hence, Form 1 was sensitive to water, and during preparation of Form 1, the water content of the solvent system should be controlled to be lower than 0.5% (volume content).

TABLE 6B

Water Activity Study Results

| Mixed solvents(V/V) | $A_w$ | Result |
|---|---|---|
| MeOH/water (100/0) | 0 | Form 1 |
| MeOH/water (99.5/0.5) | 0.010 | Form 1 |
| MeOH/water (99/1) | 0.021 | Form 1 + 2 |
| MeOH/water (97/3) | 0.065 | Form 2 |
| MeOH/water (95/5) | 0.1058 | Form 2 |

TABLE 6B-continued

| Water Activity Study Results | | |
|---|---|---|
| Mixed solvents(V/V) | $A_w$ | Result |
| MeOH/water (90/10) | 0.1998 | Form 1 + 2 |
| MeOH/water (86/14) | 0.2679 | Form 1 + 2 |
| MeOH/water (80/20) | 0.3598 | Form 1 + 2 |

Example 8. Solubility Studies in Bio-Relevant Media

Solubility of Form I of free acid, Form 1 and Form 2 of potassium salt, and Form A of sodium salt were tested in water and in bio-relevant media of Simulated Intestinal Fluid (SIF), Simulated Gastric Fluid (SGF), Fasted State Simulated Intestinal Fluid (FaSSIF), and Fed State Simulated Intestinal Fluid (FeSSIF) at 37° C. up to 24 hours. About 12 mg of the sample was weighed into sample vials and then 1.5 mL of each media was added to make suspensions respectively. All suspensions were shaken at 37° C. with 200 rpm. At 0.5, 2 and 24 hours, about 500 μL of each suspension was filtered and the filtrate was analyzed by HPLC to test the solubility. pH of the filtrate was measured, and the filter cake obtained at 2 or 24 hours was analyzed by XRPD.

Solubility of free acid of Compound 1 was very low in all tested media.

Solubility of the salts of Compound 1 showed pH dependency solubility profile. The solubility increased with increasing of pH. However, solubility of both salts in SIF was lower than in FaSSIF and FeSSIF, which was believed to be due to the presence of bile salt in the latter two media. pH shift was observed during solubility test of salts in FaSSIF. Dissociation of salts was observed during solubility test. The solubility test results are shown in Table 7 below. Solubility of the sodium and potassium salts was much greater than that of the free acid.

TABLE 7

Solubility Results in Bio-relevant Media

| | | Solubility (mg/mL) | | | PH | | | |
|---|---|---|---|---|---|---|---|---|
| Sample | Media | 0.5 h | 2 h | 24 h | 0.5 h | 2 h | 24 h | XRPD |
| Free acid | SGF | <LOQ | <LOQ | <LOQ | 1.17 | 1.19 | 1.16 | unchanged |
| Form I | FeSSIF | 0.00056 | 0.001 | 0.0011 | 4.91 | 4.86 | 5.00 | Form I with extra peak |
| | FaSSIF | <LOQ | <LOQ | 0.00052 | 6.72 | 6.60 | 6.74 | unchanged |
| | SIF | <LOQ | <LOQ | <LOQ | 6.89 | 6.86 | 6.79 | unchanged |
| | Water | <LOQ | <LOQ | <LOQ | 6.48 | 6.59 | 6.44 | unchanged |
| Sodium | SGF | <LOQ | <LOQ | <LOQ | 1.24 | 1.24 | 1.24 | Free acid |
| salt | FeSSIF | 0.0011 | 0.0029 | 0.012 | 5.09 | 5.18 | 5.26 | Free acid |
| Form A | FaSSIF | 0.0013 | 0.015 | 0.013 | 7.07 | 7.33 | 8.27 | Free acid |
| | SIF | <LOQ | <LOQ | <LOQ | 7.23 | 7.60 | 7.65 | Free acid |
| | Water | 2.8 | 3.51 | 4.57 | 10.76 | 10.81 | 10.63 | Free acid + salt Form A |
| Potassium | SGF | <LOQ | <LOQ | <LOQ | 1.18 | 1.26 | 1.25 | Free acid |
| salt | FeSSIF | 0.0017 | 0.0089 | 0.013 | 5.06 | 5.21 | 5.24 | Free acid |
| Form 1 | FaSSIF | <LOQ | 0.013 | 0.0064 | 7.03 | 7.36 | 8.29 | Free acid |
| | SIF | <LOQ | <LOQ | <LOQ | 7.52 | 7.52 | 7.44 | Free acid |
| | Water | 5.79 | 5.28 | 5.15 | 11.02 | 11.00 | 10.57 | Free acid |
| Potassium | SGF | <LOQ | <LOQ | <LOQ | 1.35 | 1.25 | 1.25 | Free acid |
| salt | FeSSIF | 0.0041 | 0.013 | 0.022 | 5.09 | 5.24 | 5.17 | Free acid |
| Form 2 | FaSSIF | 0.0011 | 0.015 | 0.0070 | 7.04 | 7.49 | 7.90 | Free acid |
| | SIF | <LOQ | <LOQ | <LOQ | 7.43 | 7.51 | 7.46 | Free acid |
| | Water | 4.63 | 6.69 | 6.71 | 10.49 | 10.62 | 10.42 | Free acid |

*LOQ is 0.5 μg/mL.

Example 9. Solid State Stability Studies

Appropriate amount of free acid Form I, potassium salts Form 1 and Form 2, and sodium salt Form A were placed at 60° C. and 40° C./75% RH for 7 days. At 0 and 7 days, the samples were dissolved in diluent to prepare a solution of 0.5 mg/mL for HPLC purity analysis. Solid samples were analyzed by XRPD to check the crystal form.

The results were summarized in Table 8. No obvious degradation and no form change occurred under testing conditions. The free acid and the salts were chemically and physically stable at 40° C./75% RH and 60° C. for 7 days. It was also noted from Table 8 that by converting the free acid into its potassium salt, the purity was improved to over 99% by HPLC area. Converting the free acid to its sodium salt also improved purity, but not to the same extent as that of the potassium salt.

TABLE 8

Stability Evaluation Results

| Sample | Initial Purity (Area %) | Purity at Day 7 (Area %) 40° C./ 75% RH | 60° C. | XRPD 40° C./ 75% RH | 60° C. |
|---|---|---|---|---|---|
| Free acid Form I | 96.45 | 96.42 | 96.47 | Unchanged | Unchanged |
| Sodium salt Form A | 97.98 | 98.02 | 98.01 | Unchanged | Unchanged |
| Potassium salt Form 1 | 99.23 | 99.29 | 99.50 | Unchanged | Unchanged |
| Potassium salt Form 2 | 99.04 | 98.97 | 99.07 | Unchanged | Unchanged |

Example 10. Polymorph Screening of Potassium Salt of Compound 1

Potassium salt of Compound 1 (Form 1) was used as a starting material for polymorph screening using several technics: slurry, cooling crystallization, and anti-solvent precipitation, etc.

In the slurry study, the initial potassium salt Form 1 was slurried in either a single solvent or a mixture of solvents. In the single solvent slurry studies, 11 solvents (ethanol (EtOH), 2-propanol (IPA), isobutyl acetate (IBuAc), 2-butanone (MEK), tetrahydrofuran (THF), acetonitrile (ACN), tert-butyl methyl ether (MTBE), acetone, toluene (Tol), ethyl acetate (EA), isopropyl acetate (IPAC), or n-Heptane (Hept)) were used with a concentration of 15 mg/mL. The suspensions of potassium salt Form 1 were kept stirring at RT or 50° C. for 3 days, respectively. Solid samples were collected by filtration and analyzed by XRPD. If a new XRPD pattern was identified, the sample was further analyzed by DSC and TGA. No new form was found.

For mixed solvent slurry studies, appropriate amount of potassium salt Form 1 was suspended in selected solvent at a concentration of 50 mg/mL and the suspensions were kept stirring at RT for 4 days or at 50° C. for 1 day. The solvents used are DMF/EA (1/1), acetone/water (19/1), ACN/IPAC (1/1), THF/IBuAC (1/1), EtOH/cyclohexane (1/1), and ACN/MTBE (1/1). Any solid obtained was collected by filtration and characterized. Form 1 was obtained from most solvents and Form 2 was obtained from solvents with water. No new crystal form was found.

In anti-solvent addition study, appropriate amount of potassium salt Form 1 was dissolved in a selected solvent, and the resulting solution was added into an anti-solvent dropwise. The anti-solvent system used included (1) DMSO as the solvent (4V), and IBuAc (36V), acetone (36V), water (16V), isobutanol (36V), ACN (36V), or EA(36V) as the antisolvent; (2) MeOH/DCM (1/1, 60V) as the solvent, heptane (45V), ACN, IPAC, or MTBE as the antisolvent; (3) THF/water (19/1, 20V) as the solvent, cyclohexane, ACN, MTBE, MEK, IPA, or IPAC as the antisolvent. The solutions or suspensions were kept stirring at room temperature for about 10 minutes to overnight, depending on the rate of precipitation, and then the solids were filtered and analyzed by XRPD. Form 1 was obtained under the condition of DMSO or MeOH/DCM as the solvent. Using THF/water as the solvent, three new XRPD patterns were found, and Form 2 was observed in one condition as well.

TABLE 9

Summary of Results of Anti-Solvent Addition

| Solvent | Anti-solvent | Result (RT) |
|---|---|---|
| DMSO (4 V) | IBuAC (36 V) | K salt Form 1 |
| | Acetone (36 V) | K salt Form 1 |
| | Water (16 V) | Free acid Form I |
| | Isobutanol (36 V) | K salt Form 1 |
| | ACN (36 V) | K salt Form 1 |
| | EA (36 V) | K salt Form 1 |
| MeOH/DCM (1/1, 60 V) | Heptane(45 V) | K salt Form 1 |
| | ACN | K salt Form 1 |
| | IPAC | K salt Form 1 |
| | MTBE | K salt Form 1 |
| | Heptane | K salt Form 1 |
| THF/water (19/1, 20 V) | Cyclohexane | Turn to sticky |
| | ACN | New crystal form, assigned as Form 3 |
| | MTBE | Nearly amorphous |
| | MEK | K salt Form 2 |
| | IPA | New crystal form, assigned as Form 4 |
| | IPAC | New crystal form, assigned as Form 5 |

Slow Evaporation: 10 to 15 mg of potassium salt Form 1 was added into glass vials, and then solvents were added to prepare solutions. The resulting solutions were filtered and the filtrates were placed at RT with pinhole cap. After solvent was evaporated to dry, solid obtained was characterized. Two new XRPD patterns were found and identified as mixed forms of Form 1 and Form 2, and Form 1 and Form 6, respectively. No new form was found through evaporation of binary solvents. Form 1 was obtained in most solvents. The results were summarized in Table 10.

TABLE 10

Summary of Results of Slow Evaporation

| Solvents | Conc. (mg/mL) | After Evaporation |
|---|---|---|
| MeOH/DCM (1/1) | 15 | Nearly amorphous |
| MeOH/DCM/Acetone (1/1/4) | 5.6 | Mixture of Form 1 and 2 |
| MeOH/DCM/THF (1/1/2) | 8.3 | Nearly amorphous |
| MeOH/DCM (3/1) | 8.3 | Nearly amorphous |
| MeOH/DCM/Isobutanol (1/1/2) | 8.3 | Mixture of Form 1 and Form 6 |
| THF/Water (19/1) | 10 | Glassy |

Cooling Crystallization: 10 mg of potassium salt Form I was added into a glass vial, then 1 mL of each selected solvent was added and kept stirring at 60° C. for 2 hours. The suspensions were filtered at 60° C. and filtrates were slowly cooled to RT under stirring and kept stirring overnight at RT. Any solid was collected by filtration and determined by XRPD. Solvent system used include methanol, EtOH/DCM (8/2), EtOH, MeOH/water (9/1), isobutanol/water (19/1), CAN, THF, and Acetone. A new XRPD pattern was found in isobutanol-water (19/1), assigned as Form 6. K salt Form 1 was also obtained through cooling crystallization in EtOH-DCM.

Form 6 was also prepared by the following procedure: 30 mg of potassium salt Form 1 was added into 1.5 mL of isobutanol/water (19/1), and the suspension was kept stirring at 60° C. for 2 h. The mixture was then cooled to RT slowly and continued stirring at RT for 3 days. The solid was collected by filtration and characterized.

Forms 3-6 were characterized as below.

Form 3: TGA showed 9.2% of weight loss from RT to 200° C., corresponding to the endothermic peak at 137 to 162° C. in DSC curve. Multiple thermal events were observed by DSC. 2.8% of THF and 1.9% of ACN were detected by NMR. Form 3 might be a solvate/hydrate.

Form 4: TGA showed 14.3% of weight loss from RT to 140° C., corresponding to the endothermic peak at 74 to 104° C. in DSC curve. The melting peak of the desolvated form was observed at 298 to 304° C. by DSC. 1.1% of THF and 10.4% of IPA were detected by NMR. Form 4 might be a solvate/hydrate.

Form 5: TGA showed two steps of weight loss from RT to 250° C. with a total weight loss of 10.9%. Multiple thermal events were observed by DSC. 0.8% of THF and 6.2% of IPAc were detected by NMR. Form 5 might be a solvate/hydrate.

Form 6: 1 mol of isobutanol was detected by NMR, corresponding to the weight loss in TGA curve. There were two endothermic peaks in DSC, and the first peak was due to desolvation and the second one was due to melting. Form 6 was determined as an isobutanol solvate. After heated to 200° C. by TGA, Form 6 was converted into Form 1.

The following Table 11 summarizes various polymorphs obtained from this example.

TABLE 11

Characterization Results of Different Forms

| Form Solvation | DSC, endo (Peak Temp. ° C., ΔH J/g) | TGA wt loss %/ @T (° C.) | DVS Water % at 80% RH |
|---|---|---|---|
| Form 1, anhydrate | 344, 30.9 | ~0.36/RT to 250 | 1.8% |
| Form 2, channel hydrate | 122, 20.9 broad; 312, 35.1 | ~1.18/RT to 250 | 1.6% |
| Form 3, solvate/ hydrate | 162, 66.6<br>216, 7.6<br>228, 18.0 Exo<br>306, 7.1 Exo | ~9.24/RT to 200 | / |
| Form 4, solvate/ hydrate | 103, 180.3<br>304, 19.0 | ~14.28/RT to 140 | / |
| Form 5, solvate/ hydrate | 159, 74.6<br>219, 6.3<br>228, 16.5 Exo<br>306, 6.7 Exo | ~2.16/RT to 80<br>~8.80/80 to 250 | / |
| Form 6, solvate | 104, 179.0<br>326, 27.0 | ~15.4/RT to 200 | / |

Example 11. Preparation of Calcium Salt of Compound 1

A certain amount of Compound 1 was dissolved or suspended in a solvent at 50° C. or ambient temperature (RT), and aqueous NaOH solution (1.1 eq.) was added to the suspension. After which, an aqueous $CaCl_2$ solution (1.2 eq.) was added to the reaction suspension.

| Solvent | Anti-solvent | Preparation procedure | XRPD result |
|---|---|---|---|
| MeOH (20 V) | N/A | An aqueous $CaCl_2$ solution (~1.1 eq.) was added into a sodium salt suspension in MeOH and stirred for 4 hours at 50° C. Solid was collected by filtration after cooled to RT. | Nearly amorphous |
| | | Filtrate was kept stirring at RT and solid was precipitated after 1 h. Solid was collected by filtration. | Pattern 1 |
| MeOH (20 V) | Water (16 V) | Free acid was not dissolved in MeOH, and the suspension was heated at 50° C., and turned more clear after base was added and then became turbid rapidly. Solid was not dissolved when an aqueous $CaCl_2$ solution was added. The suspension was cooled to RT and stirred for 10 min. 16 V of water was added and the mixture was stirred at RT for 30 min. Solid was collected by filtration. | Pattern 1 |
| MeOH (10 V) | Water (20 V) | | Pattern 2 |

Characterization of Pattern 1: NMR showed that this solid form contains 3.7% of MeOH. TGA showed a two-step weight loss: 3.02% from RT to 130° C. and 3.67% from 130° C. to 200° C. DSC showed two endothermic peaks from 64° C. to 206° C. Pattern 1 was determined to be a solvate/ hydrate. After heated to 135° C., Pattern 1 was converted into Pattern 2.

Characterization of Pattern 2: No solvent was observed by NMR. TGA also showed a two-step weight loss: 0.5% from RT and 100° C. and 3.7% from 100° C. and 200° C. The weight loss in TGA was due to water loss and corresponding to the endothermic peak at 157 to 197° C. in DSC. Pattern 2 might be a hydrate. It was hygroscopic with 3.2% of water uptake at 80% RH and crystal form of solid remained unchanged.

Example 12. Preparation of Magnesium Salt of Compound 1

A certain amount of Compound 1 was dissolved or suspended in a solvent at 50° C. or ambient temperature (RT), and an aqueous NaOH solution (1.1 eq.) was added. After which, an aqueous $MgCl_2$ solution (1.2 eq.) was added to the reaction suspension.

| Solvent | Anti-solvent | Preparation procedure | XRPD result |
|---|---|---|---|
| DMSO (10 V) | Acetone:EA:MTBE (1:1:1, 60 V) | Sodium salt was prepared firstly and then suspended in DMSO, and an aqueous $MgCl_2$ solution (~1.1 eq.) was added. The mixture was stirred at 50° C. for 1.5 hours. After cooled to RT, acetone, EtOAc and MTBE were added sequentially and stirred for 1 h. | Sodium salt Form A |
| MeOH (20 V) | Water (16 V) | Free acid was suspended in MeOH at 50° C., and an aqueous NaOH solution was added. The suspension was stirred for 10 min, and then an aqueous $MgCl_2$ solution was added. The mixture was stirred at 50° C. for 3 h, and then cooled to RT. Water was added followed by addition of MeOH-water (1:1), and the mixture was stirred for 1 hour. | Pattern 1 |
| / | / | Pattern 1, DSC to 135° C. and 230° C. | Pattern 2 |

Characterization of Pattern 1: multiple thermal events of Pattern 1 were observed by DSC and a two-step weight loss was detected by TGA. NMR showed that there was about 9% of methanol. The sample might be a solvate/hydrate.

Pattern 2 was obtained by heating Pattern 1 to 135° C. or 230° C. during DSC/TGA studies. This pattern was determined to be an anhydrate.

The Summary and Abstract sections may set forth one or more but not all exemplary embodiments of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

With respect to aspects of the disclosure described as a genus, all individual species are individually considered separate aspects of the disclosure. If aspects of the disclosure are described as "comprising" a feature, embodiments also are contemplated "consisting of" or "consisting essentially of" the feature.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

What is claimed is:

1. The Compound 1,

1

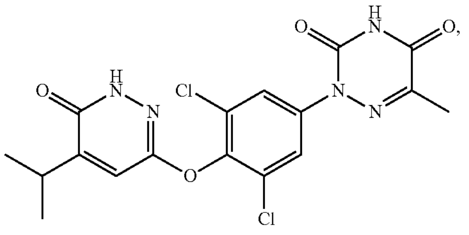

which is in a crystalline form, wherein the crystalline form is:

i) Form I of Compound 1, characterized by (1) an X-ray powder diffraction (XRPD) pattern having one or more of the following peaks: 10.8, 12.2, 12.4, 14.0, 17.1, 17.8, 22.6, 23.6, 24.6, 25.4, 26.0, and 28.8, degrees 2 theta, ±0.2°; (2) an X-ray powder diffraction (XRPD) pattern having one or more of the following peaks: 10.8, 12.2, 12.4, 14.0, 17.1, 17.4, 17.8, 20.1, 20.4, 22.6, 23.6, 24.6, 25.0, 25.4, 26.0, 28.8, 30.0, and 33.1 degrees 2 theta, ±0.2°; (3) an XRPD pattern substantially the same as shown in FIG. 1A or Table 1; (4) a Differential Scanning Calorimetry (DSC) pattern substantially the same as shown in FIG. 1B; or any combination thereof; or ii) Form II of Compound 1, characterized by (1) an X-ray powder diffraction (XRPD) pattern having one or more of the following peaks: 16.7, 17.6, 18.9, 19.8, 20.1, 20.7, 22.5, 22.7, 23.7, 24.0, and 26.5, degrees 2 theta, ±0.2°; (2) an X-ray powder diffraction (XRPD) pattern having one or more of the following peaks: 9.9, 10.8, 16.7, 17.6, 18.9, 19.8, 20.1, 20.7, 21.2, 21.6, 22.3, 22.5, 22.7, 23.7, 24.0, 24.8, 26.5, 26.7, 28.1, 29.7, and 30.7, degrees 2 theta, ±0.2°; (3) an XRPD pattern substantially the same as shown in FIG. 2A or Table 2; (4) a Differential Scanning Calorimetry (DSC) pattern substantially the same as shown in FIG. 2B; or any combination thereof.

2. The Compound 1 of claim 1, which is substantially pure.

3. A pharmaceutical composition comprising the Compound 1 of claim 1, and a pharmaceutically acceptable carrier.

4. The Compound 1 according to claim 1, which is crystalline Form I of Compound 1.

5. The Compound 1 according to claim 1, which is crystalline Form II of Compound 1.

6. The Compound 1 according to claim 4, wherein the crystalline Form I of Compound 1 is characterized by an X-ray powder diffraction (XRPD) pattern having the following peaks: 10.8, 12.2, 12.4, 14.0, 17.1, 17.8, 22.6, 23.6, 24.6, 25.4, 26.0, and 28.8, degrees 2 theta, ±0.2°.

7. The Compound 1 according to claim 5, wherein the crystalline Form II of Compound 1 is characterized by an X-ray powder diffraction (XRPD) pattern having the following peaks: 16.7, 17.6, 18.9, 19.8, 20.1, 20.7, 22.5, 22.7, 23.7, 24.0, and 26.5, degrees 2 theta, ±0.2°.

* * * * *